United States Patent [19]

Yuan et al.

[11] Patent Number: 5,455,271
[45] Date of Patent: Oct. 3, 1995

[54] TIGHT-BINDING INHIBITORS OF LEUKOTRIENE $A_4$ HYDROLASE

[75] Inventors: Wei Yuan, Sommerville, Mass.; Chi-Huey Wong, Rancho Santa Fe, Calif.; Bengt Samuelsson, Djursholm, Sweden; Benito Munoz, San Diego, Calif.

[73] Assignee: The Scripps Research Institute, La Jolla, Calif.

[21] Appl. No.: 79,239

[22] Filed: Jun. 17, 1993

Related U.S. Application Data

[63] Continuation-in-part of Ser. No. 995,789, Dec. 23, 1992, abandoned, which is a continuation-in-part of Ser. No. 900,959, Jun. 18, 1992, abandoned.

[51] Int. Cl.[6] ............................................. A61K 31/24
[52] U.S. Cl. ................. 514/538; 514/539; 514/561; 514/563; 514/541; 514/620; 514/649; 514/653; 514/654
[58] Field of Search ............................ 514/654, 561, 514/563, 538, 539, 541, 620, 649, 653

[56] References Cited

U.S. PATENT DOCUMENTS

| | | | |
|---|---|---|---|
| 4,704,464 | 11/1987 | Brunner et al. | 556/137 |
| 4,743,585 | 5/1988 | Hudspeth et al. | 514/17 |

FOREIGN PATENT DOCUMENTS

| | | |
|---|---|---|
| 0355819 | 2/1990 | European Pat. Off. |
| 355819 | 2/1990 | European Pat. Off. |
| 8802363 | 4/1988 | WIPO. |
| WO88/026363 | 4/1988 | WIPO. |

OTHER PUBLICATIONS

Medline 91083646 Dec. 14, 1990.
Ocain et al., *J. Med. Chem.*, 35(3):451–456 (1992).
Yuan et al., *Bioorg. Med. Chem. Lett.*, 1(10):551–556 (1991).
Goka et al., *J. of Medicinal Chemistry*, 34(8):2547–2557 (1991).
Bioorg. Med. Chem. Lett 1(10), pp. 551–556 Yuan et al.; Oct., 1991.
J. Med. Chem. 35(3) pp. 451–456 Ocain et al.; Feb. 7, 1992.
Journal of Medicinal Chemistry 1991, vol. 34 No. 8 pp. 2547–2557, Goka et al.; Oct. 1991.

*Primary Examiner*—José G. Dees
*Assistant Examiner*—Samuel Barts
*Attorney, Agent, or Firm*—Welsh & Katz, Ltd.

[57] ABSTRACT

Inhibitors of leukotriene $A_4$ hydrolase are disclosed, corresponding to Formula I, below:

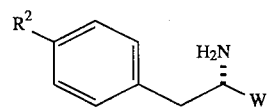

wherein the depicted —$NH_2$ group is in the (S) configuration; —W is —$CH_2SH$, —$CH_2NH_2$ or C(=Z)—Y, wherein =Z is =O, or —H and —OH; and —Y is selected from the group consisting of (a) phenyl, (b) trifluoromethylphenyl, (c) carboxyphenyl, (d) benzyl, (e) $C_1$-$C_6$ alkylenecarboxyl, (f) $C_1$-$C_6$ alkyl, (g) $C_2$-$C_6$ alkenyl, (h) $C_1$-$C_6$ alkylenephenyl and (i) —C(=O)—X—$R^1$ wherein X is O or NH and, $R^1$ is selected from the group consisting of $C_1$-$C_6$ alkyl, $C_1$-$C_6$ alkylenecarboxyl, and benzyl; $R^2$ is hydrogen, benzyloxy or 2-naphthylmethyloxy, and a pharmaceutically acceptable acid addition salt thereof. Inhibitors wherein —W is —$CH_2SH$, —$CH_2NH_2$ or C(=Z)—Y wherein =Z is =O and —Y is —C(=O)—X—$R^1$ are particularly preferred, as are those compounds wherein =Z is =O and —Y is selected from the group consisting of (a) phenyl, (b) trifluoromethylphenyl, (c) carboxyphenyl, (d) benzyl, (e) $C_1$-$C_6$ alkylenecarboxyl, (f) $C_1$-$C_6$ alkyl, (g) $C_2$-$C_6$ alkenyl, (h) $C_1$-$C_6$ alkylenephenyl. An inhibitor where —W is —$CH_2SH$, —$CH_2NH_2$ or C(=Z)—Y wherein =Z is =O and —Y is —C(=O)—X—$R^1$ is particularly preferred, as are those inhibitor compounds where =Z is =O and —Y is (a)—(h).

20 Claims, No Drawings

TIGHT-BINDING INHIBITORS OF LEUKOTRIENE A₄ HYDROLASE

This invention was made with government support under Contract CHE 8996249 awarded by the National Science Foundation and Contract GM 44154 awarded by the National Institutes of Health. The government has certain rights in the invention.

CROSS-REFERENCE TO RELATED APPLICATION

This is a continuation-in-part of application Ser. No. 07/995,789, filed December 23, 1992, now abandoned which was a continuation-in-part of application Ser. No. 07/900,959, filed Jun. 18, 1992, now abandoned.

DESCRIPTION

2. Technical Field

The present invention relates to inhibitors of the enzyme leukotriene $A_4$ ($LTA_4$) hydrolase, and particularly to α-keto- or α-hydroxy-β-amino-phenylbutyric acid ester and amide compounds, as well as β-amino-phenylpropyl mercaptans and amines.

2. Background Art

Leukotriene (LT) $A_4$ hydrolase (EC 3.3.2.6) [Samuelsson et al., *J. Biol. Chem.*, 264:19469 (1989)] is a zinc-containing monomeric enzyme (MW~70 kD) [Haeggstrom et al., *Biochem. Biophys. Res. Commun.*, 72:965 (1990)] that exhibits both epoxide hydrolase and aminopeptidase [Haeggstrom et al., *Biochem. Biophys. Res. Commun.*, 173:431 (1990); Minami et al., *Biochem. Biophys. Res. Commun.*, 173:620 (1990)] activities. The enzyme catalyzes the formation of the inflammatory mediator leukotriene (LT) $B_4$ (5S,12R-dihydroxy-6,14-cis-8,10-trans-eicosatetraenoic acid) from its natural substrate leukotriene (LT) A4 (5(S)-5,6-oxido-7,9-trans-11,14-cis-eicosatetraenoic acid), one of the physiologically important processes in the arachidonic acid biosynthetic pathway. [Samuelsson et al., *J. Biol. Chem.*, 264:19469 (1989).]

The enzyme has been purified to homogeneity from various sources as a water soluble protein [Samuelsson et al., *J. Biol. Chem.*, 264:19469 (1989)] and the genes coding for the human enzyme from placenta and spleen have been cloned and sequenced. Funk et al., *Proc. Natl. Acad. Sci. USA*, 84:6671 (1987). Although the detailed mechanism of the enzyme has not been elucidated, it is thought that the addition of a water molecule to the enzyme's substrate is general base-assisted and the role of the zinc ion is to serve as a Lewis acid to polarize epoxide ring or the carbonyl of amide, and to stabilize the negative charge developed during the reaction.

The zinc ion may also bind to the nucleophilic water molecule to facilitate the general-base catalysis. The peptidase and epoxide hydrolase activities, which occur at the same active site, may use a different general base (a carboxylate residue) as indicated in recent site-directed mutagenesis studies [Samuelsson et al., *Proc. Natl. Acad. Sci. USA*, 89:9141 (1992)]. Both enzymatic activities are activated by albumin, a characteristic distinguishing this enzyme from other $Zn^{++}$metaldohydrolases. [Oring et al., *Biochemistry*, 31:4218–4223 (1992).]

It is of great interest to develop selective inhibitors of $LTA_4$ hydrolase as potential antiinflammatory agents since $LTB_4$ is a strong proinflammatory mediator that stimulates adhesion of circulating neutrophils to vascular endothelium [McIntyre et al., *Proc. Natl. Acad. Sci. USA*, 83.:2204 (1986)] and directs neutrophil migration toward sites of inflammation. [Ford-Hutchinson et al., *Nature*, 286, 264 (1980)]. $LTA_4$ hydrolase was irreversibly inhibited by its substrate $LTA_4$ [McGee et al., *J. Biol. Chem.*, 260:12832 (1985)] and substrate analogues $LTA_3$ and $LTA_5$, [Evans et al., *J. Biol. Chem.*, 269:10966 (1985); Nathaniel et al, *Biochem. Biophy. Res. Commun.*, 131:827 (1985); Ohoshi et al., *J. Biol. Chem.*, 262:10200 (1987)]. In addition, some inhibitors of $Zn^{++}$-containing amino peptidase (e.g. Bestatin) and angiotensin converting enzyme (e.g. Captopril) are reversible inhibitors of $LTA_4$ hydrolase. Orning et al., *J. Biol. Chem.*, 266:1375 (1991).

Our study on the specificity of the amidase activities of $LTA_4$ hydrolase and the synthesis of a series of α-keto- or α-hydroxy-β-amino acid esters and amides and peptide isosteres for use to inhibit the activity of the enzyme are discussed hereinafter. This study has led to the development of a new class of transition state analog inhibitors based on both the proposed mechanism of the aminopeptidase activity and the natural substrate structure of the enzyme.

BRIEF SUMMARY OF THE INVENTION

An inhibitor compound of the invention corresponds in structure to Formula I, below:

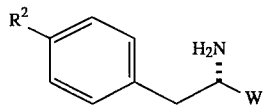

wherein —W is —$CH_2SH$, —$CH_2NH_2$ or —C(=Z)—Y, wherein =Z is =O, or —H and —OH; and —Y is selected from the group consisting of (a) phenyl, (b) trifluoromethylphenyl, (c) carboxyphenyl, (d) benzyl, (e) $C_1$–$C_6$ alkylenecarboxyl, (f) $C_1$–$C_6$ alkyl, (g) $C_2$–$C_6$ alkenyl, (h) $C_1$–$C_6$ alkylenephenyl and (i) —C(=O)—X—$R^1$ wherein X is O or NH, and $R^1$ is selected from the group consisting of $C_1$–$C_6$ alkyl, $C_1$–$C_6$ alkylenecarboxyl and benzyl; and $R^2$ is hydrogen, benzyloxy or 2-naphthylmethyloxy. The amine group (—$NH_2$) depicted in Formula I has the S configuration.

Particularly preferred compounds of Formula I are those wherein W is —$CH_2SH$ or —$CH_2NH_2$, and those of Formula II, below, wherein —W is —C(=Z)—Y, as discussed above.

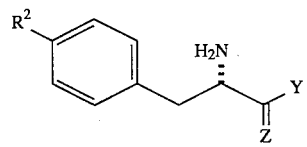

wherein R2 =Z and —Y are as discussed before

Another preferred compound of Formula II are those wherein —Y is (a)—(h) above, and where —Y is (i); i e., —C(=O)—X—$R^1$. Where —Y is —C(=O)—X—$R^1$, a compound of Formula III, below, results

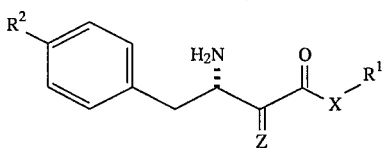

wherein the depicted —NH$_2$ group has the (S) configuration;

X is O or NH;

R$^1$ is selected from the group consisting of C$_1$–C$_6$ alkyl, C$_1$–C$_6$ alkylenecarboxyl and benzyl;

R$^2$ is hydrogen (H), benzyloxy or 2-naphthylmethyloxy; and

=Z is =O or —H and —OH.

A pharmaceutically acceptable acid addition salt of any of the above compounds of Formulas I, II or III is also contemplated.

In preferred practice, X is O. R$^1$ is preferably C$_1$–C$_6$ alkyl, or benzyl and R$^2$ is preferably benzyloxy.

An inhibitor compound more preferably contains at least two phenyl rings, and most preferably contains three phenyl rings. Thus, when R$^1$ is other then benzyl, R$^2$ is more preferably benzyloxy or 2-naphthylmethyloxy. Most preferably, an inhibitor compound contains an R$^1$ benzyl group and an R$^1$ benzyloxy group. Where =Z contains single bonds to a hydrogen and a hydroxyl, it is preferred that the hydroxyl group have the (S) configuration, so that preferred α-hydroxy-β-amino inhibitor compounds have the (2S,3S) configuration.

More preferably, =Z is =O so the compound is an α-keto-β-amino acid ester or amide, with an ester being preferred over an amide. A more preferred compound corresponds in structure to Formula IV, below, wherein R$^1$, R$^2$ and X are as above, with the above preferences A pharmaceutically acceptable acid addition salt of a compound of Formula IV is also contemplated.

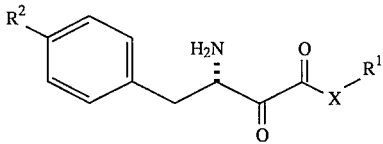

A pharmaceutical composition containing leukotriene A$_4$ hydrolase-inhibiting amount of a before-described compound dissolved or dispersed in a pharmaceutically acceptable diluent is also contemplated.

A process for inhibiting the activity of a leukotriene A$_4$ hydrolase is also contemplated. Here, the process is carried out by admixing the enzyme, its substrate and an inhibiting amount of a before-described inhibitor compound in an aqueous medium under biochemical reaction conditions, and maintaining that admixture under those conditions for a time period sufficient for the enzyme's activity to be inhibited. The inhibitor compound is preferably supplied via an above composition.

DETAILED DESCRIPTION

I. The Compounds

An inhibitor compound of the present invention can be viewed as a derivative of 2-amino-3-phenylpropane. Each compound has the 2-amino (or α-amino) group in the (S) configuration.

One embodiment of a contemplated inhibitor is (2S)-2-amino-3-phenylpropyl mercaptan or its 4'-benzylether. The latter, 2-amino-3-(4'-benzyloxy) phenylpropyl mercaptan, Compound 27, is a most preferred compound herein, as is its dimer Compound 27a. Another contemplated inhibitor is (2S)-3-[4-(2-naphthylmethyloxy)phenyl]-1,2-diamino-propane HCl, Compound 60, as is the corresponding 4'-benzyloxy compound, Compound 61.

In other embodiments of the invention, the 1-position of the propyl group is derivatized as a carbonyl group (C=O) or as a hydroxyl group (OH), with still further groups bonded to the remaining valence of the 1-position carbon atom. In a compound of these embodiments, the propyl 1-position carbon atom is shown as C(=Z)—Y, wherein =Z is the carbonyl oxygen (=O) or hydrogen and hydroxyl (—H and —OH), and —Y is the group that is bonded to the remaining valence of the propyl 1-position carbon atom.

In one aspect, —Y is a carboxylic acid ester or amide group, making the contemplated inhibitor or derivative of 3-amino-2-hydroxy-4-phenylbutanoic acid (APHA) where =Z is —H and —OH, or 3-amino-2-oxo-4-phenylbutanoic acid where =Z is =O. The 2-hydroxyl group of an APHA derivative can be in either (2S) or (2R) configuration, with the (2S) configuration being preferred. It is more preferred that the 2-hydroxyl group of such a derivative be oxidized to a keto or oxo group. When viewed as a 4-phenylbutanoic acid derivative, the before-mentioned (S)-configured amine group is in the 3-position and can be referred to as a β-amino group.

Thus, a contemplated later-discussed inhibitor compound is a (3S)-amino-2(R or S)-hydroxy-4-phenylbutanoic acid ester or amide or a (3S)-amino-2-keto-4-phenylbutanoic acid ester or amide. The 2- and 3-positions are also referred to herein as the α- and β-positions of the molecule, respectively.

The 4-phenyl portion of APHA can be a phenyl group itself, can be a 4'-(benzyloxy)-phenyl group or a 4'-(2-naphthylmethyloxy) group. Thus, the 4-phenyl group can have a 4'-substituent, referred to hereinafter as R$^2$ in the structural formulas that follow that can be hydrogen (H), benzyloxy or 2-naphthylmethyloxy. A 2-naphthylmethyloxy group has the structure —O—CH$_2$-naphthalene, where the —CH$_2$— group is bonded to the 2-position of the naphthyl ring.

Because carboxylic acid ester or amide such as a contemplated APHA derivative can be the reaction product of a carboxylic acid and an alcohol or amine, the carbon-containing group derived from the alcohol or amine can be referred to as the alcohol or amine portion of the ester or amide, respectively. That alcohol or amine portion, referred to as R$^1$ in Formulas I–IV and VII–VIII hereinafter, can be selected from the group consisting of C$_1$–C$_6$ alkyl (as above), carboxyl C$_1$–C$_6$ alkyl, and benzyl.

C$_1$–C$_6$ Alkyl groups are well known and include methyl, ethyl, isopropyl, sec-butyl, cyclopentyl, hexyl, 2-methylpentyl, cyclohexyl and the like.

A carboxyl C$_1$–C$_6$ alkyl group is an alkyl group as before-discussed that itself further includes a substituent carboxyl group. A carboxyl C$_1$–C$_6$ alkyl group can also more precisely be referred to as a C$_1$–C$_6$ alkylenecarboxyl group to clarify that the alkylene group is bonded to the oxygen or nitrogen atom of the ester or amide and to the carboxyl group. The contemplated groups include the α-carbon, carboxyl and side groups of the naturally occurring amino acids as well as their D-isomers. Indeed, a D- or L-amino acid can be used to form a contemplated amide inhibitor. Contemplated $C_1$–$C_6$ alkylenecarboxyl groups thus include carboxymethyl (carboxymethlene; —$CH_2CO_2H$), carboxyethyl (carboxyethylene; —$CH_2CH_2CO_2H$), 2-carboxybutyl [2-carboxybutylene; —$CH_2$—CH ($CO_2H$) $C_2H_5$], 3-carboxycyclopentyl (3-carboxycyclopentylene;

and the like.

In the embodiments noted before wherein the 1-position of the propyl group is derivatized as a carbonyl group or as a hydrogen and hydroxyl group with still further groups bonded to the 1-position; i.e., where that propyl 1-position carbon is C(=Z)—Y, those further groups can be selected from a number of moieties. Exemplary of those moieties are phenyl, trifluoromethyl, carboxyphenyl, benzyl, $C_1$–$C_6$ alkylenecarboxyl, $C_1$–$C_6$ alkyl, $C_2$–$C_6$ alkenyl and $C_1$–$C_6$ alkylenephenyl.

The trifluoromethyl and carboxyphenyl groups can be substituted in the ortho, meta or para positions of the phenyl ring, but meta and para are preferred. $C_1$–$C_6$ Alkyl and $C_1$–$C_6$ alkylenecarboxy groups are as discussed before. A $C_2$–$C_6$ alkenyl group is an ethyleneically unsaturated $C_2$–$C_6$ alkyl group. Exemplary groups include ethylenyl, 2-propylenyl, 4-pentylenyl, cyclohex-3-enyl and the like. A $C_1$–$C_6$ alkylenephenyl group is $C_1$–$C_6$ alkylene group bonded to the carbon shown in C(=Z)—Y, the 1-position carbon atom, and to a phenyl ring.

Thus, a preferred contemplated inhibitor compound has a structure corresponding to Formula I, below,

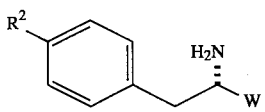

wherein —W is —$CH_2SH$, —$CH_2NH_2$ or —C(=Z)—Y, wherein =Z is =O, or —H and —OH; and —Y is selected from the group consisting of (a) phenyl, (b) trifluoromethylphenyl, (c) carboxyphenyl, (d) benzyl, (e) $C_1$–$C_6$ alkylenecarboxyl, (f) $C_1$–$C_6$ alkyl, (g) $C_2$—$C_6$ alkenyl, (h) $C_1$–$C_6$ alkylenephenyl and (i) —C(=O)—X—$R^1$ wherein X is O or NH, and $R^1$ is selected from the group consisting of $C_1$–$C_6$ alkyl, $C_1$–$C_6$ alkylenecarboxyl and benzyl; and $R^1$ is hydrogen, benzyloxy or 2-naphthylmethyloxy. The amine group (—$NH_2$) depicted in Formula I has the S configuration.

Particularly preferred compounds of Formula I are those wherein —W is —$CH_2SH$ or —$CH_2NH_2$, and those of Formula II, below, wherein —W is —C(=Z)—Y, as discussed above,

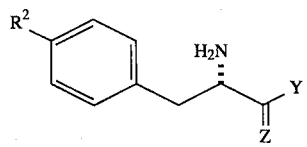

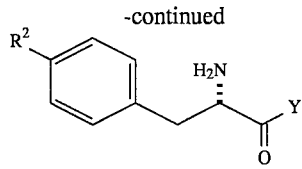

wherein $R^2$, =Z and —Y are as discussed before, with Rpreferably being other than hydrogen and =Z preferably being =O. —Y is most preferably $C_1$–$C_6$ alkylenephenyl. Compounds that include the structural preferences above for Formula II are included among those of Formula IIa, above.

Another group of preferred compounds of Formula II are those wherein —Y is (a)—(g) above, and where —Y is (h); i.e., —C(=O)—X—$R^1$. Where —Y is —C(=O)—X—$R^1$, a compound of Formula III, below, results

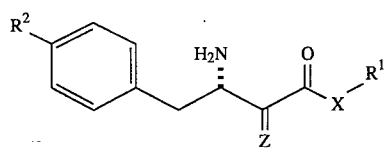

wherein =Z is =O, or —H and —OH;
X is O or NH, and $R^1$ is selected from the group consisting of $C_1$–$C_6$ alkyl, $C_1$–$C_6$ alkylenecarboxyl and benzyl; and $R^2$ is hydrogen, benzyloxy or 2-naphthylmethyloxy.

Where =Z is —H and —OH, it is preferred that the —OH group have the (S) configuration. Of the $R^1$ groups, benzyl is presently preferred, whereas benzyloxy is presently preferred as the $R^2$ group.

In examining the above structural formulas it is noted that =Z can be one of two entities; i.e., a doubly bonded oxygen (an oxo group) or a hydroxyl and a hydrogen. Thus, the two bonds shown to Z indicate the two valences from the carbon atom taken up by the Z entity, and not necessarily a double bond, except where =Z is an oxo group.

It is more preferred that an inhibitor compound contain at least two phenyl rings, four such rings being permitted by a prior formula in which the naphthalene-containing moiety is counted as two phenyl rings. It is most preferred that an inhibitor contain at least three phenyl rings. Thus, it is more preferred that when $R^1$ is other than benzyl, that $R^2$ be benzyloxy or 2-naphthylmethyloxy. Most preferably, an inhibitor compound contains both an $R^1$ benzyl group and an $R^2$ benzyloxy group so that the inhibitor contains three phenyl rings. Esters; i.e., compounds where X is O, are also presently preferred over amides.

A more preferred compound is an α-keto-β-amino compound derivative of APHA whose structure corresponds to Formula IV, below, wherein $R^1$ $R^2$ and X are as above, with the same preferences for those groups noted above.

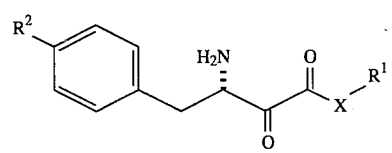

Following the preference for $R^2$ being benzyloxy, a preferred inhibitor of the invention has a structure that corresponds to Formula V, below, wherein W is as defined before.

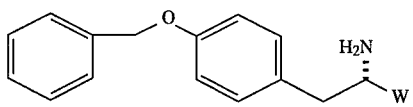

Following the preference that =Z be =O, a particularly preferred compound having a structure corresponding to Formula II has a structure corresponding to Formula VI, below, wherein —Y is as defined before.

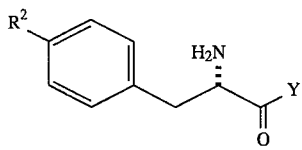

Following the preference that X be oxygen, O, another group of particularly preferred inhibitors of Formulas III and IV has a structure of Formulas VII and VIII, respectively, below, wherein $R^1$, $R^2$ and =Z are as before defined.

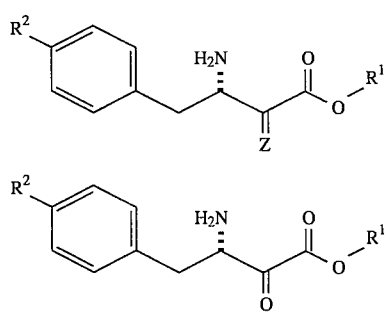

An inhibitor compound can also be present as a pharmaceutically acceptable acid addition salt. Typically, where the ester or amide is electrically neutral at physiological pH values, e.g. pH 7.2–7.6, or at another pH value at which it is utilized or prepared, the β-amino group is present as an acid addition salt. Exemplary acids from which the salts can be prepared are well known to workers skilled in the art and include HCl, HBr, HI, $H_2SO_4$, $NaHSO_4$, $H_3PO_4$, $KH_2PO_4$, $C_1$–$C_{18}$ carboxylic acids such as formic, acetic, butyric, maleic, fumaric, oleic, stearic, palmitic, lactic, citric, and tartaric acids as well as benzoic acid. Where $R^1$ includes a carboxyl group, a compound is typically present as a zwitterion.

II. Compound Syntheses

Syntheses of an inhibitor described herein is straightforward. Detailed syntheses for particular compounds, or physical data for those compounds are provided hereinafter.

αHydroxy-β-amino acids were prepared from the corresponding α-amino acids. A representative synthesis of N-t-butyloxycarbonyl-(2RS,3S)-3-amino-2-hydroxy-phenylbutanoic acid [abbreviated as N-BOC-(2RS,3S)-APHA] methyl esters Compound 32S and 32R is illustrated in Scheme 1, below.

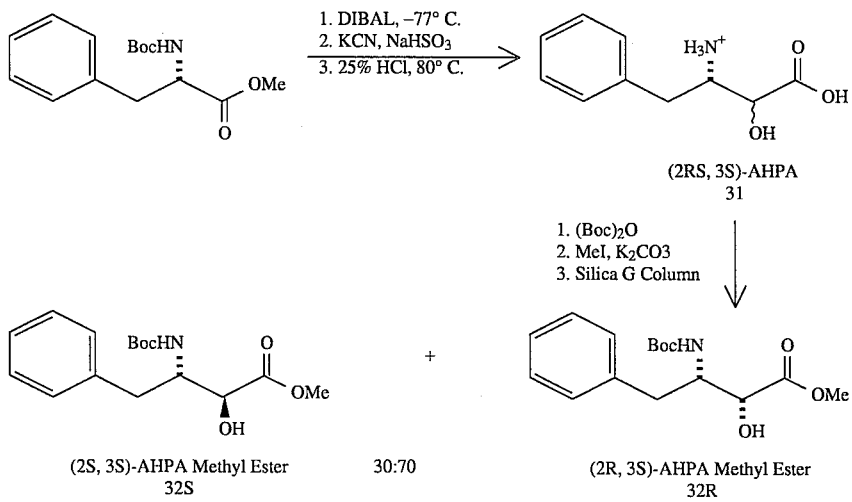

Thus, (2RS,3S)-APHA (Compound 31) was converted to N-BOC-(2RS,3S)-APHA methyl ester [Yuan et al., *Bioorg. & Med. Chem. Lett.*, 1:551 (1991)] and the diastereomers were separated on silica gel to give N-BOC-(2R,3S)-AHPA and N-BOC-(2S,3S)-AHPA methyl esters Compounds 32S and 32R. The stereochemistry at the 2-position was assigned by comparison of (2S,3R)-AHPA isopropyl ester to the published data. Iizuka et al., *J. Med. Chem.*, 33:2707 (1990).

Similar procedures were followed to prepare (Compound 34S) (the configuration of the 2-position was assigned tentatively with confidence based on the inhibitory activities of two isomers) and Compound 34R in Scheme 2, below. Compound 34R was then converted into Compound 35R, and thereafter into Compound 26, as is also shown in Scheme 2.

Scheme 2

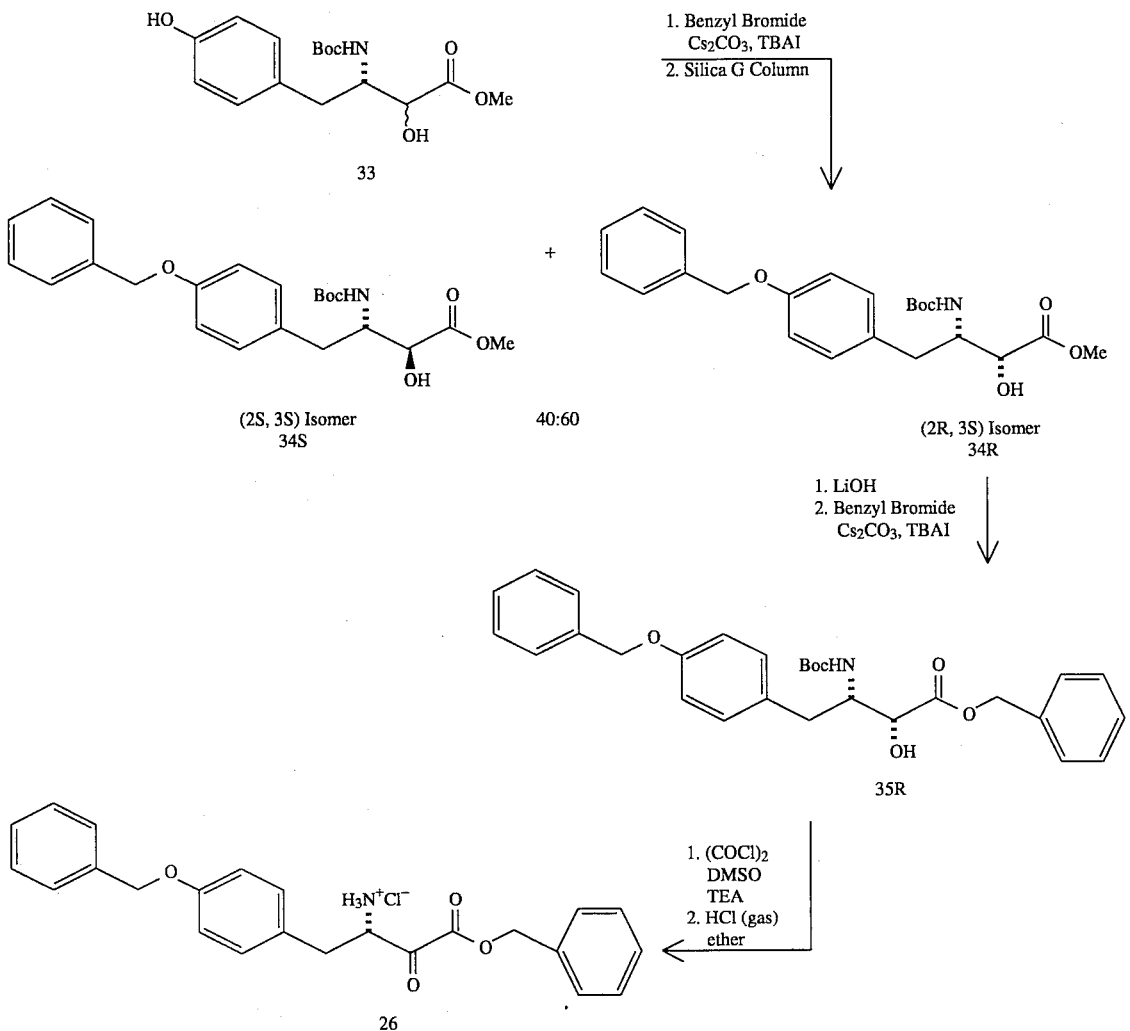

Other esters and amides contemplated herein can be prepared using Compound 34R as a starting material using standard ester-alcohol or ester-amine interchange reactions in which the alcohol portion of an ester is replaced by another alcohol or amine, respectively, to form a corresponding new ester or amide. The resulting compounds that are analogous in structure to Compound 35R can then be oxidized and deblocked to form a preferred αketo-β-amine inhibitor compound.

The dipeptides (Compounds 7, 8, 9 and 10) were made by DCC-mediated coupling of the corresponding carboxylic acids followed by deprotection. The α-keto Compounds 21, 22, 25 and 26 were prepared from the corresponding alcohol via Swern oxidation [Mancuso et al., *J. Org. Chem.*, 43:2480 (1978)] followed by deprotection, as noted before in Scheme 2 for Compound 26.

Contemplated inhibitor compounds where —Y is other than a carboxylic acid, ester or amide can be prepared using the chemistry outlined below in Schemes 3 or 4, below beginning with Weinreb amide Compounds 36 or 39. [*Nahm et al., Tetrahedron Lett.*, 22:3815–3818 (1981); Angelastro et al., *J. Org. Chem.*, 54:3913–3916 (1989).]With these syntheses, the Weinreb amide is first recited with a Grignard reagent to form the keto group that is adjacent to the S-configured amino group.

Scheme 3

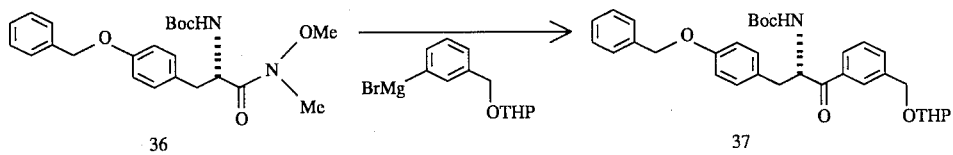

-continued
Scheme 3

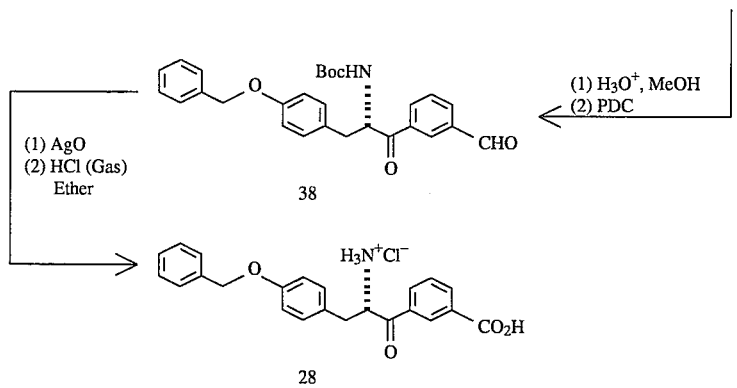

In Scheme 3 the Grignard reagent included a marked or blocked functional group, a tetrahydropyranyl (THP)-blocked benzyl alcohol. The THP group of adduct Compound 37 was removed by use of an acid (HCl) in methanol, and the resulting Boc-protected benzyl alcohol was oxidized to the aldehyde of Compound 38 using pyridinium dichromate (PDC). The Boc-protected aldehyde of Compound 38 was then oxidized with silver oxide to form the corresponding phenyl carboxylic acid, and that carboxylic acid treated with HCl gas in ether to remove the Boc group and form the HCl salt of Compound 28.

Scheme 4 is shown below.

As is seen from Scheme 4, the Weinreb amide Compound 39 (N-Boc-L-phenylalanine-N-methoxy-N-methylamide) was the starting material for two specific inhibitors herein, Compounds 44 and 45. Thus, enroute to Compound 44, Compound 39 was reacted with benzyl magnesium chloride in step a to form Compound 40 and 98 percent yield. Compound 40 was reduced in step b with NaBH$_4$ in anhydrous methanol (MeOH) at −23° C. to provide Compound 41 in 80 percent yield. Compound 41 was deblocked with trifluoroacetic acid (TFA) and then treated with 1N HCl from which the HCl salt of Compound 44 was obtained in 88 percent yield in step c.

Scheme 4

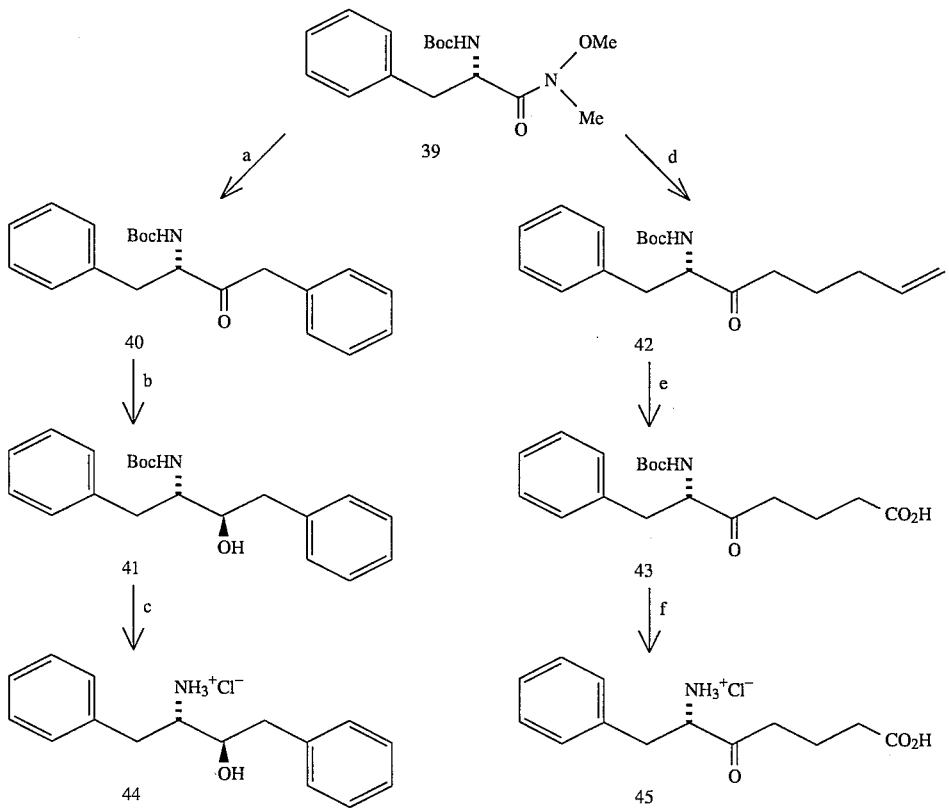

On the right-hand side of Scheme 4, Compound 39 was reacted with pentene magnesium bromide in step d to form Compound 43 in 97 percent yield. A deblocked derivative of Compound 42 is a compound of the invention wherein —Y is $C_2$–$C_6$ alkenyl. Oxidation of Compound 43 in step e with $NaIO_4$ and $KMnO_4$ provided Compound 43 in 78 percent yield. Compound 43 was converted to Compound 45 as discussed for the conversion of Compound 41 to Compound 44, in 88 percent yield in step f.

A similar reaction to those shown in Scheme 4 was used to prepare Compound 54, shown hereinafter. This reaction started with the Weinrab amide of 4'-(benzyloxy)-N-Boc-L-tyrosine (Compound 52) that was reacted in THF with 3-phenylpropane magnesium bromide to form the corresponding N-Boc phenyl-substituted ketone, Compound 53. Removal of the Boc group with HCl gas in ether provided Compound 54.

An exemplary synthesis for Compound 26 is shown in Scheme 5, hereinafter. Thus, N-Boc-L-tryosine (Compound 46) was reacted with benzyl bromide in DMF provide Compound 47, which was recovered, dissolved in THF and reduced with $LiBH_4$ to provide Compound 48. Reaction of Compound 48 in dichloromethane with tosyl chloride (TsCl) and a catalytic amount of DMAP and triethylamine provided tosylate Compound 49. That compound was reacted with potassium thioacetate in DMF to provide thioester Compound 50, whose acetyl group was cleaved with hydroxide in ethanol to provide the N-Boc mercaptan Compound 52. Removal of the N-Boc blocking group with HCl gas in ether provided Compound 27.

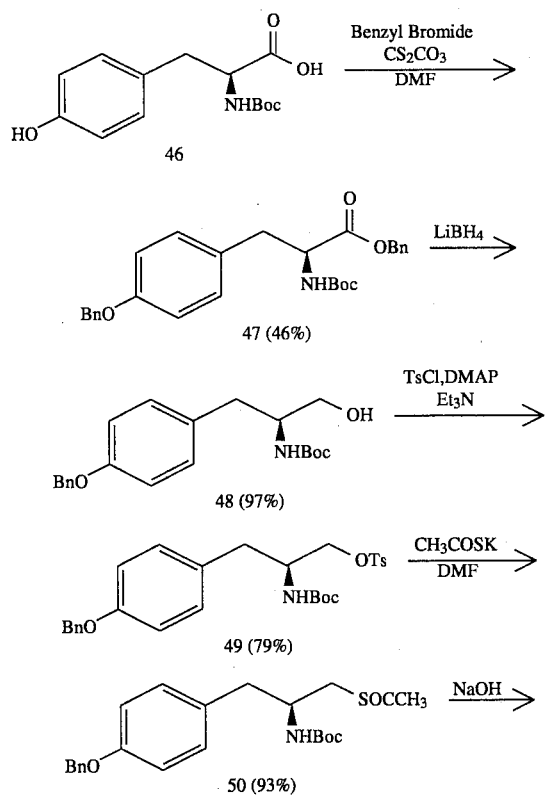

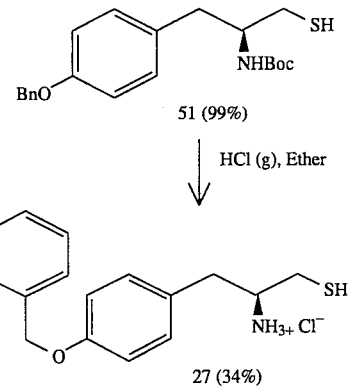

The disulfide of Compound 27, Compound 27a, is also useful herein as a prodrug form of Compound 27. Thus, administration of Compound 27a in vitro in the presence of a mild reductant such as dithiothreitol provides Compound 27. Similarly, administration of Compound 27a in vivo provides Compound 27 by body fluid reductants.

Compound 27a was prepared from Compound 50, by cleavage of the acetyl group and oxidation of the mercaptan with iodine ($I_2$) in ethanol (EtOH) to provide the disulfide Compound 51a. Compound 51a was then deblocked to provide Compound 27a. These steps are shown in Scheme 5a, below.

More generally, Compound 27a is one of group of compounds whose structures correspond to Formula IX, below, where $R^2$ is as before described.

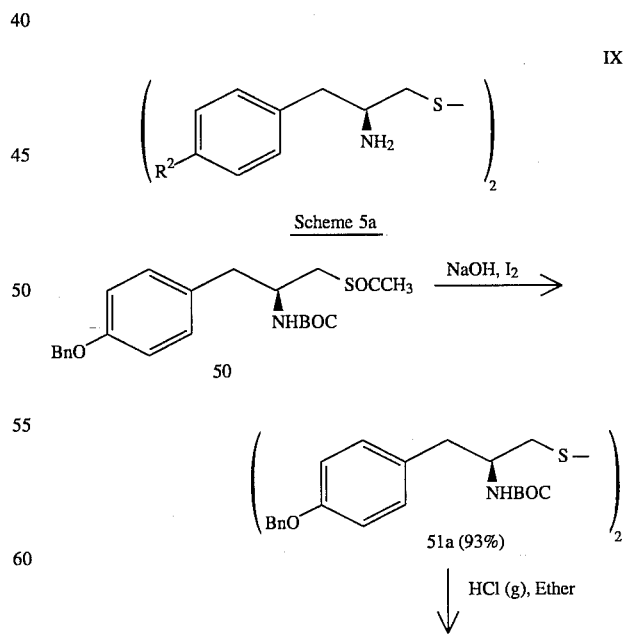

-continued

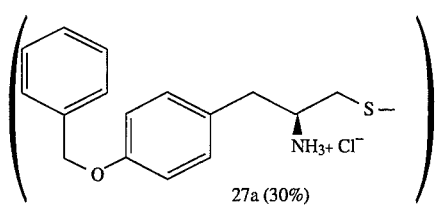

27a (30%)

Scheme 6, hereinafter, illustrates the synthesis of Compound 60. Compound 57 was prepared in a manner similar to that discussed before for Compound 49, except that 2-(bromomethyl)naphthalene was used instead of benzyl bromide to provide a 2-naphthylmethyloxy group (R), and mesyl chloride was used instead of tosyl chloride to provide a mesylate group (Ms). Compound 57 was reacted with sodium azide in DMF to provide Compound 58, whose azido group was reduced with $LiAlH_4$ in THF to provide the N-Boc amino compound, Compound 59. The Boc group was removed as before to provide the diamino hydrochloride (Compound 60).

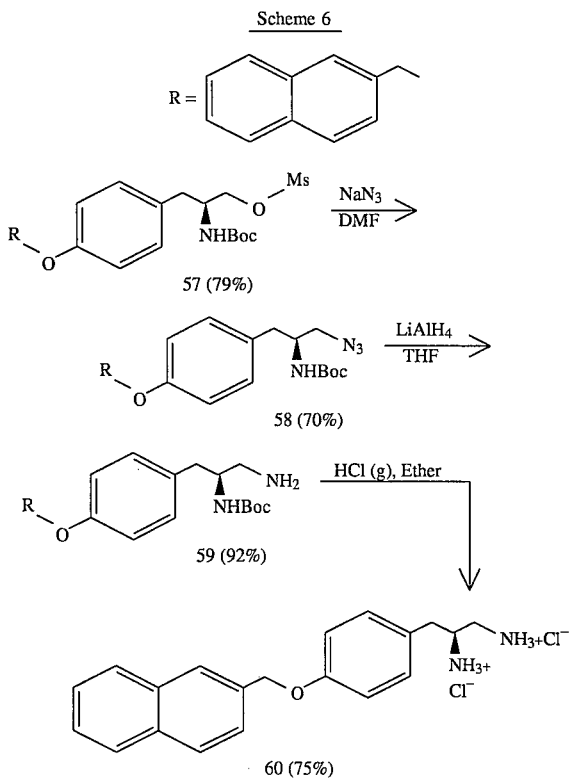

Compound 61, below, can readily be prepared from Compound 49 or its mesylate rather than tosylate derivative by reaction with sodium azide in DMF, followed by $LiAlH_4$ reduction and treatment of the resulting product with HCl gas in ether.

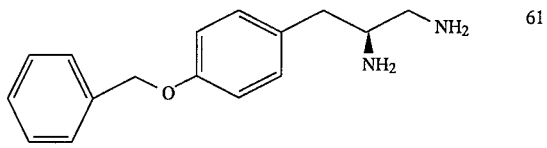

61

It should be readily apparent that the remaining compounds of Formulas I–VIII can be prepared by use of the reactions of the above schemes and analogous reactions to those shown, all of which are well known to skilled workers in organic synthesis.

III. Pharmaceutical Compositions

A pharmaceutical composition is contemplated that contains a before-described compound or its acid addition salt of the invention as active agent. A pharmaceutical composition is prepared by any of the methods well known in the art of pharmacy all of which involve bringing into association the active compound and the carrier therefor. For therapeutic use, a compound or salt of the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier or diluent.

A carrier or diluent is a material useful for administering the active compound and is "pharmaceutically acceptable" in the sense of being compatible with the other ingredients of the composition and not deleterious to the recipient thereof. As used herein, the phrases =37 physiologically tolerable" and "pharmaceutically acceptable" are used interchangeably and refer to molecular entities and compositions that do not produce an allergic or similar untoward reaction, such as gastric upset, dizziness and the like, when administered to a mammal. The physiologically tolerable carrier and diluent can take a wide variety of forms depending upon the preparation desired for administration and the intended route of administration.

As an example of a useful composition, a compound or salt of the invention (active agent) can be utilized, dissolved or dispersed in a liquid composition such as a sterile suspension or solution, or as an isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds or salts can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences,* Mack Publishing Co., Easton, Pa. (1980).

An active agent can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, *Methods in cell Biology*, Vol. XIV, Academic press, New York, N.Y. (1976), p.33 et seq.

An active agent can also be used in compositions such as tablets or pills, preferably containing a unit dose of the compound or salt. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills are preferably also provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose" as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

Actual dosage levels of an inhibitor compound or its salt in the compositions of the invention can be varied to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of a contemplated compound or its salt administered to a host in a process discussed hereinafter in single or divided doses can be in amounts, for example, of from about 0.001 to about 100 mg/kg body weight daily and preferably 0.01 to 10 mg/kg/day. Unit dosage compositions can contain amounts of submultiples thereof as may be used to make up the daily dose. It will be understood, however, that the specific dose level for any particular patient or host mammal such as a mouse, rat or rabbit will depend upon a variety of factors including the body weight, general health, sex, diet, time and route of administration, rates of absorption and excretion, combination with other drugs and the severity of the condition being treated.

For in vitro studies where the enzyme is present at about 1.4 µg/mL, final concentrations of about 1 mM to about 0.01 µM can be used, with higher concentrations being used in the pharmaceutical composition as desired to the limits of solubility or dispersibility. It should also be understood by a skilled worker that buffer and other salts that would not be pharmaceutically acceptable for use in vivo can be used in a pharmaceutical composition that is utilized for in vitro studies.

IV. Processes

A process of inhibiting the activity of leukotriene $A_4$ ($LTA_4$) hydrolase is also contemplated. In accordance with that process, that enzyme, its substrate and an inhibitor compound disclosed herein are admixed in an aqueous composition under biochemical reaction conditions, with the inhibitor compound being present in an amount sufficient to inhibit that enzyme. The resulting admixture is maintained under those conditions for a time period sufficient for the $LTA_4$ hydrolase to be inhibited.

Where enzyme inhibition is carried out in vitro, the aqueous composition is typically water containing appropriate buffers and other salts, if desired, that do not themselves inhibit the enzyme and are conducive to a reaction catalyzed by leukotriene $A_4$ hydrolase, as are well known. The temperature at which the inhibition is studied can be from above the freezing point of the resulting admixture to a temperature below the denaturation temperature of the enzyme. Typically, the temperature is about 10° to about 40° C., with ambient room temperature of about 20°–25° C. most usually being used. The in vitro pH value usually used is between about 6.5 and about 8.5, with a pH value of about 7.5 to about 8.0 being preferred. The above conditions of buffer, salt concentration (osmolity), pH value and temperature are well known in biochemistry and are referred to herein as biochemical reaction conditions.

Typical in vitro maintenance times depend upon the enzyme and substrate concentrations and upon the specific biochemical reaction conditions utilized, as is well known for enzyme kinetics studies. Usual times for maintenance range from minutes to hours.

For in vitro use, inhibition of leukotriene $A_4$ hydrolase can be monitored by reaction with the enzyme's natural substrate, leukotriene $A_4$. More conveniently, however, inasmuch as the active site for the epoxide hydrolase and aminopeptidase activities are the same, a small molecule substrate, such as a p-nitroanilide of an amino acid can be used as the substrate and hydrolysis of the amide bond can be followed spectrophotometrically by production of yellow p-nitroaniline. An inhibition of at least about 25 percent of the enzyme's activity can be used as an endpoint in a study. More frequently, a 50 percent inhibition ($IC_{50}$) value is obtained. $K_i$ value determinations provide another means for assaying inhibition.

For in vivo use, the temperature, pH value and osmolality (biological reaction conditions) are those of the host mammal to which the compound is administered. Inasmuch as the biochemistry of life for a given host mammal is carried out at those values, administration in vivo is also carried out under biochemical reaction conditions. Maintenance time in vivo is a function of the natural degradation and excretion times for a given host with a given inhibitor. Thus, the inhibitor is maintained within the host mammal such as a mouse, rat, rabbit, dog or human until it is consumed or excreted by natural bodily processes.

For in vivo use, inhibition of the activity of leukotriene $A_4$ hydrolase is monitored by the lessening of the degree of inflammation. Standard assays for the lessening of inflammation are well known and are exemplified in U.S. Pat. Nos. 5,095,104; 4,687,781; 4,251,520; 3,784,701; 3,766,263; and 3,714,226, whose disclosures are incorporated by reference. Inasmuch as the product ($LTB_4$) of the enzyme's action on its substrate ($LTA_4$) stimulates migration of neutrophils toward sites of inflammation, well known assays for the relative numbers or amount of neutrophils at a site of inflammation can also provide evidence for inhibition of the enzyme's activity in vivo, as can assays for neutrophil chemotaxis. See, for example, U.S. Pat. No. 5,095,104, whose disclosures are incorporated by reference.

In view of the effect of inhibiting the activity of $LTA_4$ hydrolase in vivo provides a lessened inflammatory response, another embodiment of the above process is a process for treating inflammation in a host mammal such as was noted before having inflammation. In accordance with this embodiment, a host mammal having inflammation is administered a $LTA_4$ hydrolase-inhibiting amount of a before-discussed inhibitor compound or its pharmaceutically acceptable salt to produce a reduction of the degree of inflammation in that host mammal. As noted previously, the amount administered in a single administration can be a submultiple of the total amount. In addition, multiple administrations over a period of several days, weeks or months are also contemplated, particularly for treating conditions of chronic inflammation such as arthritis.

Results

Several amino acid amides were assayed as substrates for $LTA_4$ hydrolase. Yuan et al., *Bioorg. & Med. Chem. Lett.*, 1:551 (1991). It was found that only L-enantiomers were substrates, and L-alanine p-nitroanilide was the best (Table 1, below). D-Alanine p-nitroanilide was not acceptable.

TABLE 1

Comparison of Kinetic parameters to $LTA_4$ Hydrolase-Catalyzed Hydrolysis of $LTA_4$ and Amide Substrates

| Substrate | $K_m$(μm) | $V_{max}$(nmol/min/mg) | $k_{cat}/K_m$(M$^{-1}$x$^{-1}$) |
|---|---|---|---|
| $LTA_4$ | 7.6[b] | 572[b] | $9.0 \times 10^4$ |
| L-Lysine p-nitro-anilide | 100 | 30 | $3.5 \times 10^2$ |
| L-Ala p-nitroanilide | 500 | 530 | $1.2 \times 10^3$ |
| D-Ala p-nitroanilide | — | 0 | — |
| L-Arg p-nitroanilide | 200 | 135 | $7.5 \times 10^2$ |
| L-Pro p-nitroanilide | 100 | 135 | $1.5 \times 10^3$ |
| L-Leu p-nitroanilide | 300 | 135 | $5.0 \times 10^2$ |

[a]Determined in 50 mM Tris-Cl, pH 7.6, in the presence of 0.1 M NaCl, $\epsilon_{410nm}$ for p-nitroaniline = 8850 M$^{-1}$cm$^{-1}$
[b]For native $LTA_4$ hydrolase, values of $K_m$ and $V_{max}$ ranging between 7–30 μM and 1.7–3.0 μmol/min/mg, respectively, have been reported using $LTA_4$ as substrate. Radmark et al., Adv. Prostaglandin, Thromboxane and Leukotriene Res., 20:35 (1990).

The inhibition activity of bestatin against $LTA_4$ hydrolase prompted the study of other L- and D-phenylalanine-derived norstatine-type of inhibitors. Without wishing to be bound by theory, it is thought that the aminopeptidase activity of $LTA_4$ hydrolase is mechanistically like that of $Zn^{++}$-containing thermolysin or aminopeptidase. The norstatine type of peptide isosteres, therefore, should be good inhibitors. The inhibition by Captopril may be due to a strong interaction between the SH group of the inhibitor and the zinc ion at the enzyme's active site.

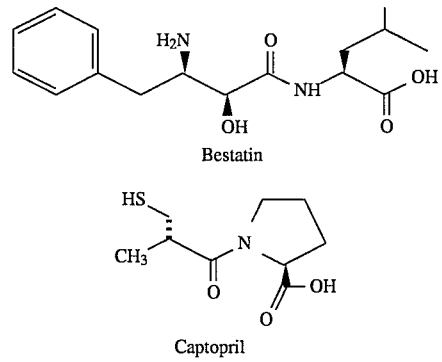

Bestatin

Captopril

Inhibitors having structures based on the proposed amidase activities were synthesized and evaluated against $LTA_4$ hydrolase purified from human leukocytes with L-alanyl p-nitroanilide as substrate. Initial studies [Yuan et al., *Bioorg. & Med. Chem. Lett.*, 1:551 (1991)] of four 3-amino-2-hydroxy-4-phenylbutanoic acid (AHPA) methyl ester stereoisomers, Compounds 1, 2, 3 and 4, below, revealed that the configuration at both 2- and 3-positions are important for inhibitory activity.

The isomer (2S, 3S)-AHPA methyl ester, Compound 2, was the most potent with an inhibition constant $K_i$ =50 μM. The other three isomers, (2R,3S), (2S,3R) and (2R, 3R)-AHPA methyl ester Compounds 1, 3 and 4, exhibited poor or no inhibition.

A free amino group was necessary as N-Boc-2S, 3S)-AHPA methyl ester showed no inhibition activity. Hydrolysis of the methyl ester to free acids (see Compounds 5 and 6) resulted in a loss of their inhibition potency. The inhibition activity was improved in the case where the C-terminus of (2S, 3S)-AHPA was coupled to L-leucine or glycine ($IC_{50}$ =20 μM for Compound 7 and 15 μM for Compound 8), but became worse when coupled to β-alanine (Compound 10, $IC_{50}$ =80 μM).

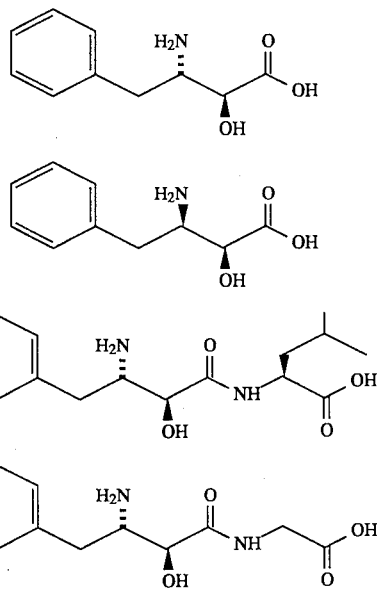

Although (2S,3R)-AHPA methyl ester, Compound 3, exhibited no activity to this enzyme, its amide derivative of L-leucine (Bestatin) is a potent inhibitor ($IC_{50}$ =4 μM). Orning, J. Biol. Chem., 266:1375 (1991). The β-alanine derivative of Compound 2 (Compound 9), however, is a weaker inhibitor ($IC_{50}$ =100 μM) than Bestatin, indicating the possible involvement of another moiety in binding. Coupling of Compound 2 with D-leucine did not improve the inhibitory potency.

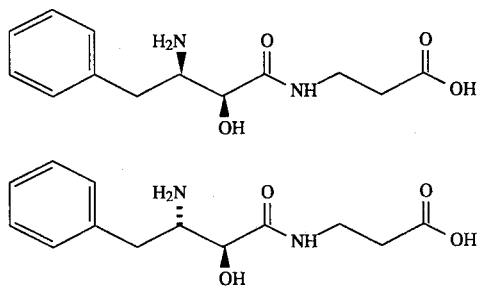

It is thought that the mode of inhibition of these AHPA derivatives is similar to that of aminopeptidase with Bestatin where the free amine and the OH group coordinate to the zinc ion. Burley, et al., Proc. Natl. Acad. Sci., 88:6916 (1991); Bartlett et al., Science, 235:569 (1987); Tronrud et al., Science, 235:571 (1987); Christianson et al., Acc. Chem. Res., 22:62 (1989); Breslow et al., Proc. Natl. Acad. Sci., 80:4585 (1983); Izquierdo-Martin et al., J. Am. Chem. Soc., 114:325 (1992); Nishizawa et al., J. Med. chem., 20:510 (1977). The AHPA derivative OH group was therefore replaced with the SH group because thiol is a better ligand for $Zn^{++}$. Surprisingly, the two thiol Compounds 11 and 12 were poor inhibitors, similar to the results observed in the study of aminopeptidase. Ocain et al., J. Med. chem., 31:2193 (1988).

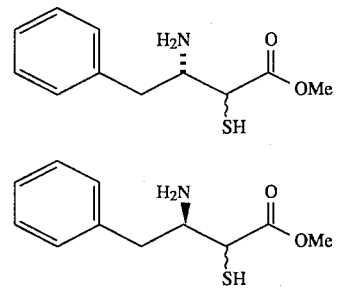

The thioamide analogs, Compounds 13-15, were also poor inhibitors. Phosphoramidate Compound 16 was synthesized and tested as a transition-state analog inhibitor. That compound was, however, similar to the case of aminopeptidase, [Giannousis et al., J. Med. Chem., 30:1603 (1987)], a much weaker inhibitor than Compound 8. The fluoroketone Compounds 17 and 18 did not inhibit the enzyme at 1 mM concentration.

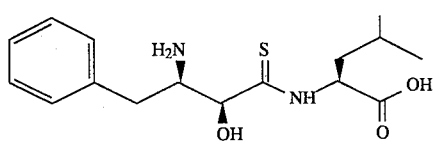

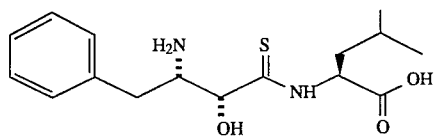

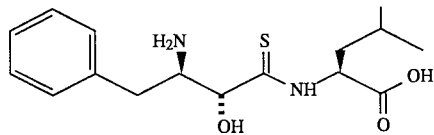

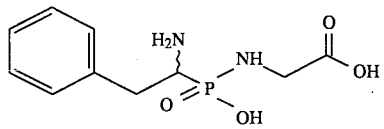

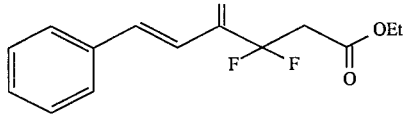

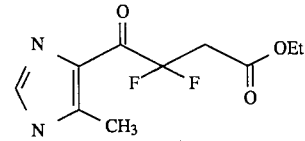

After considering the natural substrate structure and the mechanism of aminopeptidase inhibition, [Burley, et al., Proc. Natl. Acad. Sci., 88:6916 (1991); Bartlett et al., Science, 235:569 (1987); Tronrud et al., Science, 235:571 (1987); Christianson et al., Acc. Chem, Res., 22:62 (1989); Breslow et al., Proc. Natl. Acad. Sci., 80:4585 (1983); Izquierdo-Martin et al., J. Am. Chem. Soc., 114:325 (1992); Nishizawa et al., J. Med. chem., 20:510 (1977)], another class of compounds (including Compounds 21, 22, 25 through 30, 44 and 45) were prepared, that are better inhibitors than those simply based on the amidase activity.

These inhibitors contain a transition-state mimic of the enzyme-catalyzed amide cleavage as a "core" and additional complementarity components (the at least two phenyl ring aromatic moieties) that resemble the hydrophobic conjugated polyene system of the natural substrate LTA$_4$ that binds to the enzyme more tightly than do the amide substrates.

An αketo ester is preferred over an α-keto amide. [α-Keto amide inhibitors of aminopeptidase were reported by Ocain et al., *J. Med. Chem.*, 35:451 (1992). For other types of keto ester inhibitors, see Hori et al., in Peptides; Structure and Function, *Proceedings of the 9th American Petpide Symposium;* Deber et al., eds., Pierce Chemical Co., Rockford, IL. 1985 pp.819; Angelastroc et al., *J. Med. Chem.*, 23:11 (1990); Hu et al., Arch. Biochem. Biophys., 281:271 (1990)]. The reason for this preference is based on the inhibition results of Compounds 19 and 20, where the ester derivative bound more tightly than the amide.

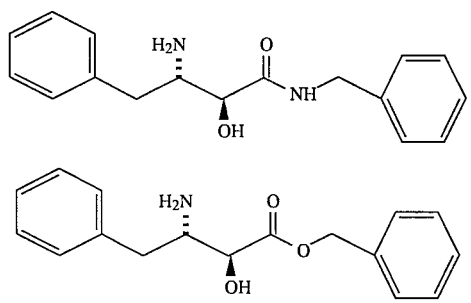

The α-keto amide with a free carboxyl group (Compound 22) was, however, a good inhibitor (IC$_{50}$ =0.5 µM) and the inhibition potency was better than the corresponding α-(S)—OH derivative Compound 7. Interestingly, although Compound 21 is comparable with Compound 2, Compound 25 (IC$_{50}$ =0.6 µM) bound to the enzyme 30 times more tightly than did Compound 23.

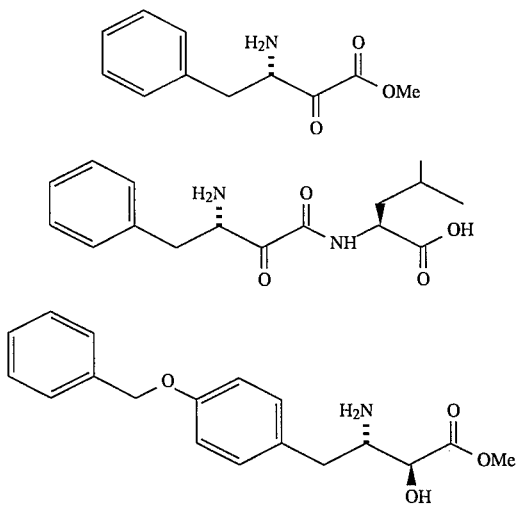

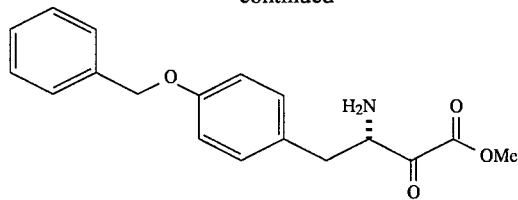

Further adjustment of the inhibitor structure at P1' and P1-P3 sites led to the development of a β-amino-α-keto ester containing three phenyl rings, Compound 26, with IC$_{50}$ =0.2 µM and K$_i$ =0.046 µM (46 nM). Both $^1$H-NMR and $^{13}$C-NMR studies indicate the β-amino-α-keto esters are completely hydrated, [For Compounds 25 and 26, the β-protons in their $^1$H-NMR's appear at about 3.9 ppm (hydrated form) in D$_2$O and about 5.0 ppm (ketone form) in DMSO; the α-carbons in the $^{13}$C-NMR's appear at about 92 ppm (hydrated form) in 10 percent D$_2$O— DMSO and at about 188 ppm (ketone form) in DMSO], which suggests that the inhibitor exists as a gem-diol bound in the enzyme active site.

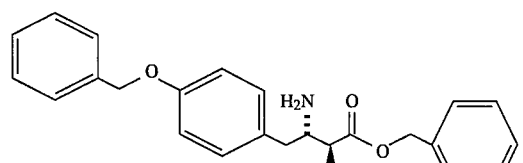

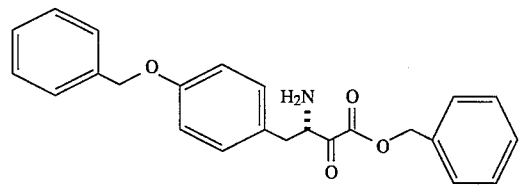

The free amino group and one of the hydroxyl groups may coordinate to the Zn$^{++}$ (as N-Boc and N-Cbz derivatives are not inhibitors) and the other hydroxyl group may interact with the general base (—CO$_2$—) via H-bonding. Unlike Bestatin and Captopril, Compounds 24, 25 and 26 are selective for LTA$_4$ binding. Those compounds are very weak inhibitors of other aminopeptidases; the IC$_{50}$ values are >100 µM for 80 µM and >100 µM for aminopeptidase M, and 80, 50 and >100 µM for cytosolic leucine aminopeptidase, respectively.

Attention was turned to the synthesis of more stable, non-peptide transition-state analog inhibitor Compounds 27–30, 44, 45, 54 and 60. These compounds, except 27 and 54, are, however, not as potent as 26, probably due to the lack of complete hydration of the carbonyl group.

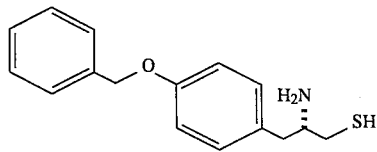

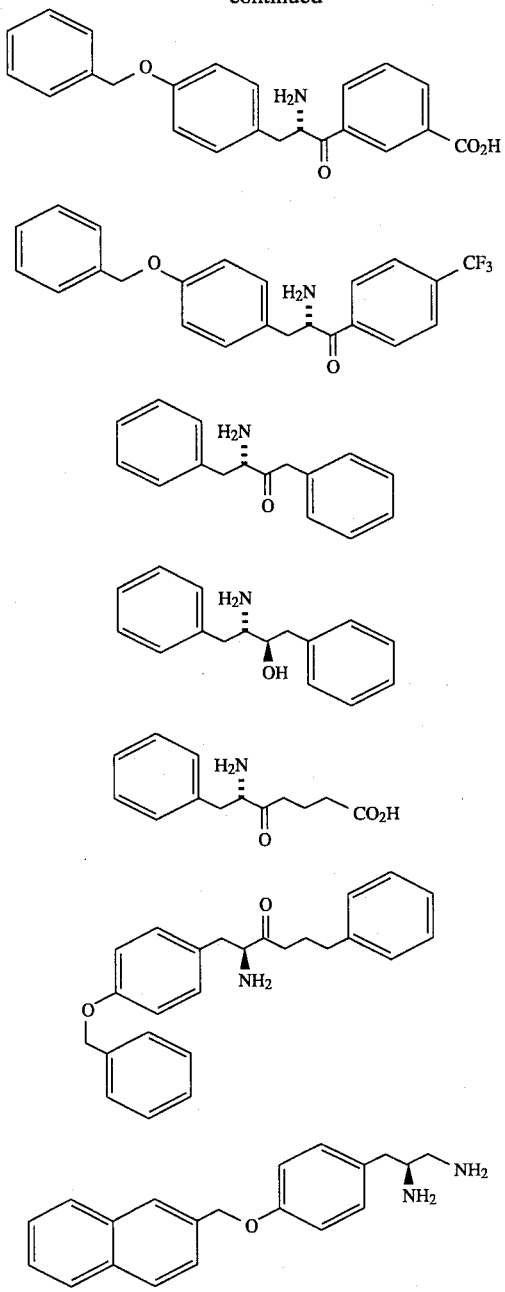

Compound 27 is so far the best inhibitor of LTA₄ hydrolase, with Compound 54 not being far behind. It inhibits the aminopeptidase activity with $K_i$ =18 nM and the epoxide hydrolase activity with $K_i$ =0.1 mM. It is a weaker inhibitor of aminopeptidase M and cytosolic leucine aminopeptidase with IC$_{50}$ =0.5 mM and >50 mM, respectively. Compound 27 probably forms a tight-binding complex in which the $Zn^{++}$ coordinates to the amine and the thiol groups. Further investigation on the mechanisms of inhibition with Compounds 26 and 27 is in progress.

Table 2, below, provides IC$_{50}$ or $K_i$ values for each of Compounds 1–30, 44, 45, 54 and 60, as well as Bestatin and Captopril.

TABLE 2

Inhibition Constants of the Listed Compounds for LTA₄ Hydrolase[a]

| Compound | $K_i$ | Compound | $K_i$ |
|---|---|---|---|
| 1 | IC$_{50}$ > 0.5 mM[b] | 18 | IC$_{50}$ > 1 mM[d] |
| 2 | 50 μM | 19 | IC$_{50}$ > 100 μM |
| 3 | NI[c] | 20 | IC$_{50}$ = 0.8 μM |
| 4 | NI[c] | 21 | IC$_{50}$ = 80 μM |
| 5 | IC$_{50}$ > 1 mM | 22 | IC$_{50}$ = 0.5 μM |
| 6 | NI[c] | 23 | IC$_{50}$ = 20 μM |
| 7 | IC$_{50}$ = 20 μM | 24 | IC$_{50}$ = 0.8 μM |
| 8 | 15 μM | 25 | IC$_{50}$ = 0.6 μM |
| 9 | IC$_{50}$ ≈ 100 μM | 26 | 46 nM |
| 10 | IC$_{50}$ ≈ 80 μM | 27 | 18 nM |
| 11 | IC$_{50}$ ≈ 250 μM | 28 | IC$_{50}$ = 3 μM |
| 12 | IC$_{50}$ ≈ 250 μM | 29 | IC$_{50}$ = 10 μM |
| 13 | IC$_{50}$ > 0.1 mM[d] | 30 | 14 μM |
| 14 | IC$_{50}$ > 9,1 mM[d] | 44 | IC$_{50}$ = 140 μM |
| 15 | IC$_{50}$ > 0,1 mM[d] | 45 | IC$_{50}$ = 20 μM |
| 16 | IC$_{50}$ ≈ 200 μM | 54 | IC$_{50}$ = 30 nM |
| 17 | IC$_{50}$ > 5 mM[d] | 60 | IC$_{50 = 0.55}$ μM |
| | | Bestatin | IC$_{50}$ = 4 μM (0.2 μM[e]) |
| | | Captopril | IC$_{50}$ = 0.07 μM[e] |

[a]All assays were performed in Tris-HCl buffer (0.05 M, pH 8.0) with L-alanyl p-nitroanilide (1.5 mM) as substrate unless otherwise indicated. LTA₄ hydrolase (1.4 μg) purified from human leukocytes was added for each assay (final volume = 1.0 mL). p-Nitroaniline formation was monitored spectrophotometrically at 405 nm. Thiol compounds were assayed in the presence of 5 mM DTT. The values shown are within ± 5 percent accuracy. Dixon plot was used to determine the $K_i$ values.
[b]Less than 50 percent inhibition was observed at this concentration.
[c]NI, no inhibition observed with 1 mM inhibitor in the assay.
[d]Less than 10 percent inhibition was observed at this concentration.
[e]Measured against L-lysine p-nitroanilide. Orning et al., J. Biol. Chem., 266:1375 (1991).

Several Further assays were conducted that illustrate the efficacy of a contemplated compound.

For the results shown in Tables 3 and 4, below, compounds were dissolved in DMSO and then diluted in Hank's BSS. Blood was drawn from a human volunteer, and a compound solution at one of three concentrations (Table 3) or a single concentration (Table 4), or solution alone (vehicle) was added to a one ml aliquot of the blood. After incubation for 15 minutes, 14 μg of calcium ionophore A-23187 (as the free acid) was added, and the incubation continued for another 15 minutes. The reactions were stopped by immersion of the containers into slush ice, and the samples were centrifuged at 11,000 ×g to pellet red cells and leukocytes. An aliquot of the plasma was then assayed for the presence of thromboxane B₂ or leukotriene B₄ by standard radioimmunoassay techniques. The data in Tables 3 and 4 are expressed as percent inhibition of eicosanoid produced in compound-treated blood compared to vehicle-treated blood.

TABLE 3

Inhibition of Thromboxane B₂(TXB₂) and Leukotriene B₄ (LTB₄)

| Compound Number | Concentration (μM) | % Inhibition TXB₂ | % Inhibition LTB₄ |
|---|---|---|---|
| 26 | 10 | 28 | 24 |
| | 3 | 7 | 17 |
| | 1 | 8 | 15 |
| 24 | 10 | 4 | 39 |
| | 3 | 17 | 44 |
| | 1 | 0 | 7 |
| 25 | 10 | 41 | 39 |

TABLE 3-continued

Inhibition of Thromboxane $B_2$ (TXB$_2$) and Leukotriene $B_4$ (LTB$_4$)

| Compound Number | Concentration (μM) | % Inhibition TXB$_2$ | % Inhibition LTB$_4$ |
|---|---|---|---|
|   | 3  | 20 | 59 |
|   | 1  | 25 | 29 |
| 10 | 10 | 19 | 15 |
|   | 3  | 21 | 39 |
|   | 1  | 12 | 14 |
| 7 | 10 | 24 | 37 |
|   | 3  | 15 | 10 |
|   | 1  | 21 | 25 |

As can be seen, the compounds assayed exhibited similar potencies. Tepoxalin, which inhibits two other reactions [cyclooxygenase production of PGD$_2$ (IC$_{50}$ =0.2 μM) and 5-lipoxygenase production of 5-HETE (IC$_{50}$ =1.29 μM)] is more potent than any compound in this table in this assay system.

TABLE 4

| Compound Number | Concentration (μM) | % Inhibition TXB$_2$ | % Inhibition LTB$_4$ |
|---|---|---|---|
| 45 | 10 | 12 | 11 |
| 30 | 10 | 6 | 15 |
| 7 | 10 | 0 | 25 |
| 29 | 10 | 0 | 10 |
| 24 | 10 | 0 | 18 |
| 21 | 10 | 0 | 8 |
| 28 | 10 | 0 | 16 |
| 27a | 10 | 24 | 100 |
| 27 | 10 | 100 | 100 |

The data of Tables 3 and 4 were taken at different times and illustrate differences in absolute percentages of inhibition for the assays as can be seen for the results for Compounds 10 and 7 in both tables. The complete inhibitions exhibited by Compounds 27 and 27 a were startling.

IC$_{50}$ Values were calculated for Compounds 27 and 27a in this assay using concentrations of about 0.3–10 μM. Those values were found to be about 0.81 μM for Compound 27a and about 1.1 μM for Compound 27, and are about those of tepoxalin in its inhibitions.

Assays of the epoxide hydrolase activity of LT$_4$ hydrolase were also conducted. The data from those studies are provided in Table 5, below, and were obtained as discussed hereinafter.

TABLE 5

Inhibition of Epoxide Hydrolase Activity

| Compound Number | IC$_{50}$ Epoxide Hydrolase (μM) |
|---|---|
| 7 | 100 |
| 8 | NI |
| 20 | 100 |
| 24 | 2.2 |
| 25 | 100 |
| 28 | NI |
| 29 | >100 |
| 27 | 0.2 |
| 30 | >100 |
| Captopril | 240 |
| Bestatin | 0.3 |

NI = No inhibition at 100 μM concentration.

LTA$_4$ hydrolase used for Table 5 results was obtained from human leukocytes and was purified to apparent homogeneity by streptomycine and ammonium sulfate precipitations, ion-exchange, hydrophobic interaction and chromatofocusing chromatographies, as described in Wetterholm et al., *Biochim. Biophys. Acta,* 1080:96–102 (1991). After the final purification step, the buffer was changed to 10 mM Tris-Cl, pH 8 by repeated centrifugation on a Centricon-30 microconcentrator (Amicon, Danvers, MA), lyophilized and stored at −20° C. SDS-PAGE was performed on a Phast system (Pharmacia) using 10–15 percent gradient gets. Bands of protein were visualized by staining with coomassie brilliant blue. Protein concentrations were determined by the method of Bradford, *Anal. Biochem.,* 72:248–254 (1976), using bovine serum albumin as standard.

The inhibition of LTA$_4$ hydrolase activity was determined by incubating purified enzyme (2.5 μg in 100 μl of 50 mM HEPES buffer, pH 8) for 30 minutes at room temperature, with the respective inhibitor dissolved in a mixture of DMF/H$_2$O (80/20, v/v). Compound 27 was dissolved in 90 percent methanol containing 10–5 mM DTT. LTA$_4$ (3 nmol) was added in 0.5 μl of THF and the reaction was permitted to proceed for 15 second prior to quenching with 200 μl methanol.

A defined amount of internal standard, prostaglantin B$_1$ (PGB$_1$; Upjohn) was added, the samples were acidified to pH 3 with 0.1M HCl, and subjected to solid phase extraction using Chromabon C$_{18}$ columns, as described in Steinhilber et al., *J. Chromatogr.,* 493:305–400 (1991). For RP-HPLC, a column (Nova-Pak C$_{18}$, 4 μm, Radial-Pak cartridge, 5×100 mm; Waters) was eluted with a mixture of methanol/water/ acetic acid (70/30/0.01; v/v/v) at a flow rate of 1.2 ml/minute. The absorbance of the eluate was monitored continuously at 270 nm. Quantitations of LTB$_4$ were made from area integration using Baseline 810 computer software (Waters) based on a standard curve obtained from analysis of known amounts of the respective compounds.

Compounds 24 and 27 were also studied for their abilities to inhibit 5- and 15-lipoxygenase using calcium ionophore A-23187-stimulated polymorphonuclear leukocytes (PMNL) in the presence of exogenous arachidonic acid. 5-Lipoxygenase activity (production of 5-HETE) was inhibited, at 1–2 log orders higher than those for inhibition of LTA$_4$ hydrolase activity. No inhibition of 15-lipoxygenase activity was noted. LTC$_4$ Synthase activity in human platelets was also not inhibited.

LTB$_4$ Formation in calcium ionophore A-23187-stimulated intact PMNL was dose dependently inhibited by Compounds 24 and 27 with IC$_{50}$ values of 100–200 nM for both substances. Thus, Compound 24 was unexpectedly much more active in this assay using intact PMNL than in assays with the isolated enzyme.

The above results illustrate the specificity of the contemplated compounds towards LTA$_4$ hydrolase as compared to other closely related enzymes in the arachidonic acid cascade. Most prior attempts to control leukotrienes have focused on 5-lipoxygenase, which converts arachidonic acid into LTA$_4$, the common substrate for both LTA$_4$ hydrolase and LTC$_4$ synthase. The demonstrated selectivity of the present compounds towards only LTA$_4$ hydrolase, which catalyzes the final and rate-limiting step in LTB$_4$ biosynthesis, can be beneficial in reducing drug side effects.

Best Mode for Carrying out the Invention

General Methods.

$^1$H-NMR spectra were obtained at 300, 400 or 500 MHz, $^{13}$C-NMR spectra were obtained at 100 or 125 MHz. All chemical shifts are reported in δ units (ppm) relative to tetramethylsilane (assigned to 0.0 ppm). Thin-layer chromatography (TLC) was performed on silica gel plates (0.25 mm, Merck) by using the following detection methods: UV, visualized under an ultraviolet lamp; $I_2$ on silica; AMA, dipped into a solution containing 5 percent ammonium molybdate, 4.2 percent $H_2SO_4$ and 0.6 percent sodium arsenate and heated on a hot plate. Flash chromatography was performed with silica gel (230–400 mesh, Merck). The following solvents were used: chloroform (C), ethyl acetate (EA), hexane (H), methanol (M or MeOH), ethanol (EtOH)

EXAMPLE 1

Method A: General Procedure for Peptide-Bond Formation

The N-deprotected amino acid (1 equivalent) was dissolved to a concentration of 0.1M in DMF, and a C-protected compound (1 equivalent, usually as a HCl salt) and HOBt (1.5–2 equivalent) were added, followed by N-methylmorpholine (1 equivalent) and DCC (1 equivalent). The mixture was stirred overnight at room temperature. The reaction mixture was diluted with ethyl acetate and the solid was removed by filtration. The filtrate was washed with 10 percent citric acid (2×), saturated sodium bicarbonate (2×), and brine. The organic layer was dried over MgSO4 and concentrated to dryness in vacuo. The final product was either directly used in the next step or purified by flash chromatography depending on the purity as judged by NMR spectra or TLC.

EXAMPLE 2

Method B: General Deprotection Procedure (1) The protected peptide was dissolved to a concentration of approximately 0.5M in 50 percent trifluoroacetic acid in dry dichloromethane and the mixture was stirred at room temperature for three hours. The solvent was removed in vacuo and the remaining trifluoroacetic acid was removed by repeated evaporation from dichloromethane in vacuo.

(2) The protected peptide was dissolved to a concentration of approximately 0.2–0.5M in ether and dry HCl (gas) was bubbled in until saturated. The reaction was stirred at room temperature overnight (about 18 hours). The solid was triturated with ether and collected by filtration.

(3) The methyl ester was dissolved in 20 percent methanol in THF to a concentration of about 0.1 M and 1.1 equivalents of lithium hydroxide dissolved in 0.5–mL water were added. The reaction progress was monitored by TLC. The reaction took about one to three hours to complete. Most solvents were removed in vacuo and the residue was dissolved in ethyl acetate. The organic layer was washed with 10 percent citric acid and then water, dried over MgSO4. The free acid was 10 obtained after removal of the solvent in vacuo.

Example 3

Method C: Preparation of N-t-Butyloxycarbonyl-AHPA (3-Amino-2-Hydroxy-4-Phenylbutanoic Acid) Methyl Ester (Scheme 1)

To a stirred solution of L-phenylalanine methyl ester (10.8 g, 50 mmol, hydrochloride salt) in 150 mL of 20 percent THF in water was added sodium bicarbonate (8.4 g, 100 mmol) at room temperature, followed by di-t-butyl dicarbonate (10.9 g, 50 mmol). The mixture was stirred at room temperature overnight (about 18 hours). The reaction mixture was extracted with ether (2×100 mL), and the ether layers were combined and dried over MgSO4. Boc-phenylalanine methyl ester was obtained as a pale yellow oil. The oil was dissolved in 70 mL dry toluene and cooled to −77° C. under nitrogen and 125 mmol diisobutylaluminum hydride (1.0M in hexane, 125 mL, 2.25 equivalent) were added in 15 minutes. Methanol (10 mL) was added immediately to quench the reaction. The reaction mixture was poured to a solution of 100 mL of 20 percent sodium potassium tartrate (Rochelle salt) and stirred at room temperature until the two layers separated. The organic layer was taken and concentrated in vacuo.

The resulting aldehyde was treated with a solution of sodium metabisulfite (14.5 g, 75 mmol) in 50 mL water and then to the emulsion was added a solution of potassium cyanide (4.9 g, 75 mmol) in 50 mL water with stirring. The reaction was stirred at room temperature for about five hours and the cyanohydrin was extracted twice with ether and the ether layer was combined and concentrated in vacuo to dryness. The residue was treated with 25 percent hydrochloric acid and the solution was stirred at 80° C. for 12 hours.

The water was removed in vacuo to give crude (2RS, 3S)-AHPA as a brown solid, which was dissolved in 100 mL of 20 percent THF in water and the pH was adjusted to about 8 by addition of 10 N NaOH solution. To the solution was added sodium carbonate (8.3 g, 100 mmol) and di-t-butyl dicarbonate (21.8 g, 100 mmol). The mixture was stirred at room temperature overnight and the pH of the reaction was adjusted to 2 with 6N HCl and extracted with ethyl acetate. The organic layer was taken and washed with 10 percent citric acid once. The product, N-t-butyloxycarbonyl-AHPA, was again extracted by 1N NaOH to the aqueous phase. The side products and other impurities were left in the organic layer. The aqueous phase was acidified to pH 2 and extracted with ethyl acetate. The ethyl acetate was removed and N-Boc-AHPA was obtained as pale yellow solid.

The solid was dissolved in 15 mL DMF, and methylated by adding potassium bicarbonate (8 g, 80 mmol) and iodomethane (11.4 g, 80 mmol). After 12 hours, the reaction was diluted with ethyl acetate and washed with 10 percent citric acid twice and then water once. Concentration of the organic layer afforded final product (8.5 g, 55 percent overall yield) as a mixture of two diastereomers (2R:2S ~7:3), which were separated by preparative TLC (2 mm, Merck about 200 mg each) by using 35 percent EA in H as solvent or by flash column (5 percent EA in H, 10 percent EA in H then 20 percent EA in H).

N-Boc-(2R,3S)-AHPA methyl ester (Compound 32R): TLC (R$_f$0.33, 25 percent EA in H, UV or AMA); $^1$H-NMR (CDCl$_3$, 300 MHz) δ1.39 (s, 9H), 2.9 (m, 2H), 3.75 (s, 3H), 4.05 (d, J=4.0 Hz, 1H), 4.25 (m, 1H), 4.78 (d, J=9 0 Hz, 1H), 7 15–7.35 (m, 5H); [a]$^{24}_D$=−7.8 5° (c =1.0, CHCl$_3$).

N-Boc-(2S, 3S) -AHPA methyl ester (Compound 32S): TLC (R$_f$0.21, 25 percent EA in H, UV or AMA); $^1$H-NMR (CDCl$_3$, 300 MHz) δ1.39 (s, 9H), 2.8 (m, 2H), 3.75 (s, 3H), 4.33 (m, two overlapped protons), 4.85 (d, J=8.0 Hz, 1H), 7.15–7.35 (m, 5H); [a]$^{24}_D$=−15.5 (c=10, CHCl$_3$).

EXAMPLE 4

(2R, 3S), (2S, 3S), (2S, 3R), (2R, 3R)-AHPA Methyl Esters (Compounds 1, 2, 3, 4)

The four isomers were made in the same way as free bases. A representative procedure is given below. 100 mg N-Boc-(2S, 3S) -AHPA methyl ester was deprotected by the general deprotecting procedure B(1). After removal of solvent, the residue was treated with 10 mL of saturated sodium bicarbonate solution and extracted with ethyl acetate (2×100 mL). The organic layers were combined with dried over $MgSO_4$. The product was obtained as a pale yellow oil (solidified at room temperature in a few days) after removal of the solvent (60 mg, 90 percent).

(2S, 3S)-APHA methyl ester (Compound 2): $^1$H-NMR ($CDCl_3$, 300 MHz) δ2.58 (m, 1H), 2.80 (m, 1H), 3.48 (m, 1H), 3.80 (S, 3H), 4.24 (d, J=3.0 Hz, 1H), 7.15–7.35 (m, 5H); $[a]^{24}_D$3.3° (c=1.2, 1N HCl).

(2S, 3R)-AHPA methyl ester (Compound 3): $^1$H-NMR ($CDCl_3$, 300 MHz) δ2.74 (m, 1H), 2.92 (m, 1H), 3.35 (m, 1H), 3.80 (S, 3H), 4.08 (d, J=3.5 Hz, 1H), 7.2–7.35 (m, 5H); $[a]^{24}_D$=+19.6° (c=0.84, 1 N HCl)

EXAMPLE 5

(2S,3S) and (2S,3R)-AHPA (Compounds 5, 6)

The two compounds were made in the same manner as trifluoroacetic acid salt. N-Boc-(2S, 3S)-AHPA methyl ester (200 mg, 0.65 mmol) was demethylated according to Method B(3) to give the corresponding free acid. The acid was deprotected by following Method B(1) to give (2S, 3S)-AHPA as a trifluoroacetic acid salt (160 mg, 80 percent):

(2S, 3S)-APHA $^1$H-NMR ($D_2O$, 400 MHz) δ2.98 (m, 2H), 4.0 (m, 1H), 4.50 (d, J=3.0 Hz, 1H), 7.20–7.40 (m, 5H); $[a]^{24}_D$=−2.2°(c=0.67, 1N HCl).

(2S, 3R)-AHPA: $^1$H-NMR ($D_2O$, 300 MHz) δ3.0 (m, 2H), 3.88 (m, 1H), 4.25 (d, J=3.0 Hz, 1H), 7.20–7.40 (m, 5H). $[a]^{24}_D$=+11.8°(c=1.02, 1N HCl).

EXAMPLE 6

The following compounds were prepared by coupling appropriate N-Boc acids and amino acid t-butyl esters according to Method A and deprotected by following Method B(1).

A: (2S, 3S)-AHPA-L-Leu (Compound 7) [Nishizawa et al., *J. Med. Chem.*, 20:510 (1977)](trifluoroacetic acid salt): $^1$H-NMR ($D_2O$, 400 MHz) δ0.90 (m, 6H), 1.6–1.8 (m, 3H), 2.95 (d, J=13 Hz, 2H), 4.02 (m, 1H), 4.25 (m, 1H), 4.56 (d, J=3.0 Hz, 1H), 7.25–7.40 (m, 5H); $[a]^{24}_D$=−26.5°(C=1.0, $H_2O$).

B: (2S, 3S) -AHPA-Gly (Compound 8) (trifluoroacetic acid salt): $^1$H-NMR ($D_2O$, 400 MHz) δ3.0 (m, 2H), 3.89 (s, 2H), 4.02 (m, 1H), 4.55 (d, J=3.0 Hz, 1H), 7.15–7.35 (m, 5H); $[a]^{24}_D$=−19.0°(c=0.1, $H_2O$) HRMS: 253.1183 (M+H)$^+$, calcd. for ($C_{12}H_{16}N_2O_4$+H) 253.1188.

C: (2S, 3S) -AHPA-β-Ala (Compound 10) (trifluoroacetic acid salt): $^1$H-NMR ($D_2O$, 300 MHz) δ 2.45 (t, J=7.8 Hz, 2H), 2.88 (m, 2H), 3.25 (t, J=8.0 Hz, 2H), 3.95 (m, 1H), 4.38 (d, J=3.0 Hz, 1H), 7.2–7.4 (m, 5H); $[a]^{24}_D$=−16.7°(c=1.02, $H_2O$) HRMS: 267.1345 (M+1)$^+$, calcd for ($C_{13}H_{18}N_2O_4$+H) 267.1345.

EXAMPLE 7

Endothiodipeptides (Compounds 13 and 15)

Boc-(2S, 3R)-AHPA methyl ester (500 mg, 1.6 mmol) was dissolved in a solution of 2,2-dimethoxypropane (15 mL) and p-toluenesulfonic acid (100 mg, dried azeotropically from benzene). After stirring at room temperature for 36 hours, the reaction was diluted with ethyl acetate and the organic layer was washed with saturated $NaHCO_3$ (2×) and water, concentrated in vacuo to dryness. Purification of the residue on silica gel (5 percent EA, 45 percent H in C, then 10 percent EA in H) afforded the isopropylidene methyl ester as a pale yellow oil which was hydrolyzed by following the general deprotection procedure to afford an acid as a white solid (470 mg, 88 percent for two steps). The general procedure for peptide formation was followed to effect the coupling of the acid (425 mg, 1.27 mmol) and L-leucine t-butyl ester (HCl salt, 310 mg, 1.5 mmol), giving a product as a white solid (505 mg, 79 percent) after purification on silica gel (5 percent EA, 20 percent H in C).

The protected dipeptide product (150 mg, 0.3 mmol) was dissolved in 7 mL dry benzene and the Lawesson's reagent (75 mg, 0.18 mmol, Aldrich) was added. The resulting solution was stirred at 88° C. (bath temperature) for 1.5 hours in a capped flask. TLC showed a complete reaction (starting material $R_f$=0.61, product $R_f$=0.71, 25 percent ethyl acetate in hexane, UV or AMA). The reaction was concentrated in vacuo and the residue was purified on preparative TLC (2 mm, Merck, 30 percent EA in H) to afford the protected endothiodipeptide as a pale yellow oil (150 mg, 96 percent); MS: 512 (M+1)$^+$. The thio compound was treated with 10 mL trifluoroacetic acid and stirred at room temperature for five hours, then 2 mL methanol were added to the solution and stirred at 70° C. (bath temperature) for 6 hours. The solvent was removed in vacuo and the residue lyophilized from benzene to give product Compound 13 as a white solid (75 mg, 77 percent). NMR and TLC showed the existence of other diastereomer Compound 15, perhaps the racemization took place at the carbon α to thioamide during the thionation. The product (35 mg) was further purified by silica gel preparative TLC (2 mm, Merck, 30 percent methanol in chloroform, developed twice) to give pure Compounds 13 (20 mg) and 15 (8 mg).

Compound 13 (TFA salt): TLC ($R_f$0.36, 25 percent M in C, UV); $^1$H-NMR (400 MHz, $D_2O$) δ0.85 (d, 3H, J=6.4 Hz), 0.88 (d, 3H, J=6.4 Hz), 1.60–1.89 (m, 3H), 2.78 (m, 1H), 2.97 (m, 1H), 3.82 (m, 1H), 4.35 (d, 1H, J=3.0 Hz), 4.60 (m, 1H), 7.23–7.38 (m, 5H); $[a]^{22}_D$=−17.2° (c=0.87, 1H HCl); MS: 325 (M+1)$^+$.

Compound 15 (TFA salt): TLC ($R_f$0.28, 25 percent M in C, UV); $^1$H-NMR (400 MHz, $D_2O$) δ0.90 (d, 3H, J=6.4 Hz), 0.94 (d, 3H, J=6.4 Hz), 1.66–1.89 (m, 3H), 2.62 (m, 1H), 2.94 (m, 1H), 3.91 (m, 1H), 4.62 (d, 1H, J=3.0 Hz), 4.68 (m, 1H), 7.26–7.38 (m, 5H); $[a]^{22}_D$=+15.6° (c=0.15, 1H HCl ), MS: 325 (M+1)$^+$.

EXAMPLE 8

Endothiodipeptide (Compound 14)

The procedure for the preparation of Compound 14 was the same as that for the preparation of Compound 13: TLC ($R_f$0.42, 25 percent M in C, UV or AMA); $^1$H-NMR (400 MHz, $D_2O$) δ0.81 (d, 3H, J=6.5 Hz), 0.86 (d, 3H, J=6.5 Hz), 1.57 (m, 1H), 1.65 (m, 1H), 1.69 (m, 1), 2.88 (m, 2H), 3.81 (m, 1H), 4.29 (d, 1H, J=2.4 Hz), 4.65 (m, 1H), 7.20–7.35 (m, 5H); $[a]^{22}_D$=+11 1°(c=0 57, 1N HCl)

EXAMPLE 9

Preparation of Compound (a): -Triphenylmethyl-4(5)-methylimidazole-5(4)-carboxylaldehyde 4-Methyl-5-imidazolemethanol hydrochloride (1.5 g, 10 mmol, Aldrich) was dissolved in a solution of triethylamine (2.8 mL, 20 mmol), DMF (10 mL) and dichloromethane (20 mL) at room temperature, triphenylmethyl chloride (2.76 g, 9.9 mmol) was added. The resulting solution was stirred at room temperature overnight and solid came out the solution. The solid was collected by filtration and washed with $H_2O$ and ethyl acetate, air-dried to give the protected imidazole alcohol as two isomers (3.1 g, 88 percent). The protected imidazole alcohol (1.5 g, 4.2 mmol) was suspended in 30 mL dry 1,4-dioxane and the solution was heated with a hair dryer to dissolved most of the solid. Activated $MnO_2$ (1.5 g, 4×4.2 mmol, Aldrich) was added and the reaction was stirred at room temperature for 24 hours. The dark reaction solution was filtered through a Celite pad and the filtrate was concentrated in vacuo to dryness. The residue was purified on silica gel (5 percent EA, 5 percent H in C) to give the title compound as a white solid (1.0 g, 67 percent): TLC ($R_f$ 0.5, 50 percent EA in H). $^1$H-NMR (300 MHz, $CDCl_3$) δ1.85 (s, 3H, —$CH_3$), 9.9 (s, 1H, —CHO), MS: 353 (M+H)$^+$.

(b) Difluoroimidazolealcohol Analogue

The aldehyde was coupled with ethyl bromodifluoroacetate according to a published procedure. [Thaisrivongs et al., *J. Med. Chem.*, 29:2080 (1986).] Activated zinc (262 mg, 64.0 mmol) and 10 mL THF in a two-neck flask was refluxed at 75°–80° C. and 0.52 mL (4.0 mmol) ethyl bromodifluoroacetate were added through a syringe continuously over 10 seconds. The aldehyde (0.71 g, 2.0 mmol) dissolved in 5 mL $CH_2Cl_2$ and 5 mL THF was added over one minute. The resulting solution was refluxed for 15 minutes. The solvent was removed in vacuo and the residue dissolved in chloroform and the chloroform layer was extracted with 5 percent EDTA solution (pH =10) twice, dried over $MgSO_4$. Removal of chloroform gave the crude product as a white solid (0.8 g, 84 percent). The compound was used in the next step without further purification: TLC ($R_f$ 0.62, 10 percent M in C, UV or AMA).

(c) Difluoroketoneimidazole Analogue, Compound 18

The oxidation procedure was described before. [Pfitzner et al., *J. Am. Chem. Soc.*, 87:5561 (1965).] The crude alcohol (200 mg, 0.42 mmol) was dissolved in dry benzene (3 mL) and DMSO (0.15 mL, 5×0.42 mmol), DCC (435 mg, 5×0.42 mmol) and anhydrous phosphoric acid (25 mg, 0.25 mmol) were added. The mixture was stirred at room temperature for 24 hours. The solid was removed by filtration and the filtrate was concentrated in vacuo. The residue was purified on silica gel preparative TLC (2 mm, Merck, 30 percent ethyl acetate in hexane) to give the triethyl-protected difluoroketone as a white solid (105 mg, 53 percent): TLC ($R_f$'s 0.35 and 0.30, two isomers, 25 percent ethyl acetate in hexane, UV or AMA). Deprotection was done by dissolving the compound in 5 mL trifluoroacetic acid and stirring for four hours at room temperature. The acid was removed in vacuo and the residue was dissolved in 4 mL $H_2O$ (2+2 mL), filtered to remove solid. The filtrate was lyophilized to give the final product 18 as a white solid (42 mg, 82 percent). $^1$H-NMR (300 MHz, $D_2O$, hydrated and ketone forms) δ1.20 (two t, 3H, J=7.2 Hz), 2.33 and 2.52 (two s, 3H, —$CH_3$), 4.29 (two q, 2H, J=7.2 Hz), 8.53 and 8.54 (two s, 1H, aromatic H); MS (methanol as solvent), 233 (M+1)$^+$, 251 (M+18+H)$^{30,}$ hydrated form (265 (M+32+H)$^+$, hemiketal with methanol.

EXAMPLE 10

(2S, 3S)-AHPA Benzyl Amide (Compound 19

N-Boc-(2S, 3S)-AHPA (90 mg, 0.31 mmol) was coupled with benzyl amine (70 mg, 0.65 mmol) according to the Method A and deprotected by following Method B(1) 10 to give the title compound as a white solid (101 mg, overall 82 percent in two steps, trifluoroacetic acid salt). $^1$H-NMR (DMSO, 300 MHz) δ2.78 (d, J=6.8 Hz, 2H), 3.68 (m, 1H), 4.20 (d, J=8.1 Hz, 2H), 4.28 (d, J=3 Hz, 1H), 7.15–7.35 (m, 5H); MS: 285 (M+1)$^+$; [a]$^{24}_D$=−24.8°(c=0.70, AcOH).

EXAMPLE 11

Method D: General Procedure for the Preparation of Phenol Benzyl Ether or Benzyl Ester (Scheme 2).

The following preparation is typical.

(2RS,3S)-3-N-t-Butyloxycarbonylamino-2-Hydroxy-4-(4-benzyloxphenyl)-Butanoic Acid, methyl ester (Compound 34S) and its diastereomer (Compound 34R). Compound 33 (prepared from Boc-Tyr(benzyl) methyl ester according to Method C) (1.2 g, 3.7 mmol) was dissolved in 5 mL of dry DMF and $Cs_2CO_3$ (2.4 g, 7.4 mmol, Aldrich), tetrabutylammonium iodide (50 mg, Aldrich), benzyl bromide (1.2 g, 1.8×3.7 mmol) were added sequentially. The disappearance of the starting material was followed by TLC (usually took two to five hours). The reaction mixture was diluted with ethyl acetate and the organic layer was washed with water (2×), concentrated in vacuo to dryness. The residue was purified on silica G (20 percent EA in H) to give (2R, 3S) isomer (680 mg, 44 percent, white wax), (2S, 3S) isomer (450 mg, 29 percent, white wax) and a mixture of the two (260 mg, 17 percent). (2R, 3S) isomer (Compound 34R): TLC ($R_f$ 0.58, 50 percent EA in H, UV or AMA), $^1$H-NMR ($CDCl_3$, 400 MHz) δ1.38 (s, 9H), 2.84 (m, 2H), 3.73 (s, 3H), 4.05 (br s, 1H), 4.18 (m, 1H), 4.77 (d, J=10.0 Hz, 1H), 5.03 (s, 2H), 6.91 (d, J=6.8 Hz, 2H), 7.18 (d, J=8.4 Hz, 2H), 7.30–7.43 (m, 5H); (2S, 3S) isomer (Compound 34S): TLC ($R_f$ 0.44, 50 percent EA in H, UV or AMA); $^1$H-NMR ($CDCl_3$, 400 MHz) δ1.38 (s, 9H), 2.73 (m, 2H), 3.55 (s, 3H), 4.24 (br s, 1H), 4.30 (d, J=4.8 Hz, 1H), 4.82 (d, J=6.8 Hz, 2H), 5.03 (s, 2H), 6.87 (d, J=6.4, 2H), 7.10 (d, J=8.4 Hz, 2H), 7.25–7.42 (m, 5H).

EXAMPLE 12

Method E: Preparation of Compound 25

DMSO (256 mg, 3.28 mmol) was added to a solution of $(COCl)_2$ (211 mg, 1.64 mmol) in 5 mL dry $CH_2Cl_2$ at −77° C. and after being stirred at this temperature for 10 minutes, Compound 34R (170 mg, 0.41 mmol) in 5 mL of dry $CH_2Cl_2$ was added dropwise. After stirring at −77° C. for 20 minutes, the reaction mixture was treated with triethylamine (331 mg, 3.28 mmol) and the mixture was stirred at the same temperature for 10 minutes before warming up the room temperature. The reaction mixture was diluted with 20 mL of hexane and filtered to remove the salt, the filtrate was concentrated, the residue purified on silica G (25 percent EA in H) to obtain the Boc-protected Compound 25 (clear oil, 150 mg, 89 percent). The Boc group was removed by following Method B(2) to give Compound 25 as a pale yellow solid (85 mg, 67 percent, HC salt): $^1$H-NMR ($D_2O$, 400 MHz) δ2.85 (dd, J=8.1, 14.3 Hz, 1H), 3.00 (dd, J=6.8, 14.7 Hz, 1H), 3.49 (s, 3H), 3.84 (t, J=7.04 Hz, 1H), 5.18 (s, 2H), 7.03 (d, J=8.6 Hz, 2H), 7.21 (d, J=8.6 Hz, 2H), 7.37–7.50 (m, 5H); $^{13}$C-NMR (10 percent $D_2O$ in DMSO, 100 MHz) δ32.90, 52.33, 57.59, 69.10, 91.74, 114.81, 127.62, 127.69, 127.83, 127.90, 128.51, 130.55, 137.10, 157.16, 169.77; high-resolution MS: 314.1386 (M+H)$^+$, calcd for ($C_{18}H_{19}NO_4$+H) 314.1392.

EXAMPLE 13

Compound 21

The compound was prepared by oxidation of corresponding alcohol N-Boc- (2RS, 3S) -AHPA methyl ester (32) according to Method E and deprotected according to Method B(2) to give the title compound (HCl salt, pale yellow powder): $^1$H-NMR ($D_2O$, 400 MHz) $\delta 2.88$ (dd, J=8.9, 14.5 Hz, 1H), 3.12 (dd, J=6.0, 14.4 Hz, 1H), 3.65 (s, 3H), 3.89 (dd, J=6.0, 8.8 Hz, 1H), 7.30–7.43 (m, 5H); MS: 208 $(M+1)^+$, 226 $(M+H_2O+1)^+$(hydrate form).

EXAMPLE 14

Compound 22

The title compound was prepared by oxidizing the corresponding alcohol, N-Boc- (2S, 3S) -AHPA-L-Leu-t-but according to Method E and deprotected according to Method B(1) to give the title compound (trifluoroacetic acid salt, pale yellow powder): $^1$H-NMR ($D_2O$, 400 MHz) $\delta$ 0.91 (m, 6H), 1.65–1.78 (m, 3H), 2.78 (m, 1H), 3.10 (m, 1H), 3.75 (m, 1H), 4.37 (m, 1H), 7.18–7.42 (m, 5H); MS (FAB$^{31}$): 305 $(M-1)^{31}$.

EXAMPLE 15

Compound 23

The title compound was made via deprotection of the corresponding N-Boc protected Compound (34S) according to Method B (2 ) (HCl salt, white powder): $^1$H-NMR ($D_2O$, 400 MHz) $\delta 2.93$ (m, 2H), 4.08 (br m, 1H), 4.57 (d, J=2.2 Hz, 1H), 5.18 (s, 2H), 7.02 (d, J=8.4 Hz, 2H), 7 21 (d, J=8.4 Hz, 2H), 7.39–7.50 (m, 5H); $[a]^{24}{}_D$= +3.5 (c=1.0, AcOH); HRMS: 316.1550, calcd for $(C_{18}H_{21}NO_4+H)$ 316.1548.

EXAMPLE 16

Compound 24

Compound 34S (400 mg, 0.96 mmol) was demethylated according to Method B(3) to give the corresponding free acid (380 mg, 99 percent). The free acid (150 mg) was benzylated by following Method D to give the benzyl ester Compound 35S as a white solid (150 mg, 81 percent) after purification on silica G column (30 percent EA in H). The benzyl ester (100 mg) was deprotected according to Method B(2) to give the title compound (HCl salt, white powder, 75 mg, 86 percent): $^1$H-NMR ($D_2O$, 400 MHz) $\delta 2.85$ (d, J=6.9 Hz, 2H), 4.05 (br m, 1H), 4.42 (d, J=11.9 Hz, 1H), 4.57 (br s, 1H), 4.71 (d, J=12.0 Hz, 1H), 5.12 (s, 2H), 6.94 (d, J=7.8 Hz, 2H), 7.10 (d, J=8.2 Hz, 2H), 7.25–7.44 (m, 10H); $[a]^{24D}$=+3.0 (c=1.0, AcOH); HRMS: 392.1858, calcd for $(C_{24}H_{25}NO_4+H)$ 392.1861.

EXAMPLE 17

Method F: Compound 26 (Scheme 2)

The benzyl ester (RS)-35 (180 mg, 0.37 mmol) was dissolved in 8 mL dry $CH_2Cl_2$ under argon, and to this solution was added Dess-Martin reagent [Dess et al., *J. Org. Chem.*, 48:4155–4156 (1983); Burkhart et al., *Tetrahedron Lett.*, 29:3433–3436 (1988)] (400 mg, 0.94 mmol) portionwise at room temperature with stirring. After stirring at room temperature for 1.2 hours, the reaction mixture was diluted with ether (30 mL), followed by saturated $NaHCO_3$ (10 mL) and $Na_2S_2O_3$ (1.0 g in 10 mL $H_2O$), and stirred until two layers became clear. The organic layer was separated and washed with $H_2O$ and dried over $MgSO_4$. The Boc-protected Compound 26 was obtained as a pale yellow solid after removal of solvent and lyophilization. The compound was pure as judged by TLC and $^1$H-NMR and was deprotected according to Method B (2) to give Compound 26 as a white powder (HCl salt, 120 mg, 77 percent for two steps): $^1$H-NMR (20 percent $D_2O$ in DMSO, 400 MHz), $\delta 2.71$ (d, J=6.9 Hz, 2H), 3.49 (t, J=6.8 Hz, 1H) 4.67 (d, J=12 Hz, 1H), 4.86 (d, J=12 Hz, 1H), 5.03 (s, 2H), 6.86 (d, J=8.4 Hz, 2H), 7.01 (d, J=8.8 Hz, 2H), 7.25–7.38 (m, 10H); $^{13}$C-NMR (20 percent $D_2O$ in DMSO, 100 MHz) $\delta 32.85$, 57.65, 66.97, 69.12, 91.77, 114.84, 114.81, 127.57, 127.63, 127.71, 127.92, 128.30, 128.47, 128.53, 130.14, 130.52, 135.00, 137.02, 157.19, 169.23; HRMS: 390.1709 $(M+H)^+$, calcd for $(C_{24}H_{23}NO_4+H)$ 390.1705.

EXAMPLE 18

Compound 27

The title compound was prepared first as a Boc-protected disulfide dimer by following the same procedures as described [Fournie-Zaluski et al., *J. Med. Chem.*, 35:1259–1266 (1992)] and then deprotected according to the Method B (2) to give the compound as a white solid HCl salt: $^1$H-NMR ($d_4$-MeOH, 400 MHz), $\delta 2.80$ (m, 4H), 2.89 (m, 2H), 3.02 (m, 2H), 3.77 (br s, 2H), 5.06 (s, 4H), 6.99 (d, J=8.6 Hz, 4H), 7.16 (d, J=8.6 Hz, 4H), 7.32–7.45 (m, 10H), HRMS: 545.2305, calcd for $(C_{32}H_{36}N_2O_2S_2+H)$ 545.2296.

EXAMPLE 19

Method G: Compound 28 (Scheme 3)

(A) Compound 37

THP-protected 3-bromobenzylalcohol (2.71 g, 10 mmol) was added to a suspension of Mg turnings (270 mg, 11 mmol) in 20 mL dry THF under argon. The resulting solution was refluxed for three hours under argon, and the solution was cooled to room temperature. To this freshly prepared Grignard reagent solution was added Weinreb amide [Nahm et al., *Tetrahedron Lett.*, 25:3815–3818 (1981); Angelastro et al., *J. Org. Chem.*, 54:3913–3916 (1989)] (1.65 g, 4.0 mmol) portionwise under a positive argon pressure and stirred at room temperature for three hours before pouring into a saturated $NH_4Cl$ solution at zero degrees C. The product was extracted with ethyl acetate (2×) and purified on silica gel column (20 percent EA in H) to afford Compound 37 as a pale yellow oil (2.0 g, 92 percent): TLC ($R_f$0.35, 25 percent EA in H, UV or AMA); NMR ($CDCl_3$, 400 MHz), $\delta 1.42$ (s, 9H), 1.54–1.85 (m, 6H), 2.86 (dd, J=5.6, 14 Hz, 1H), 3.12 (dd, J=5.6, 14 Hz, 1H), 3.57 (m, 1H), 3.91 (m, 1H), 4.53 (m, 1H), 4.72 (m, 1H), 4.81 (m, 1H), 5.0 (s, 2H), 5.39 (d, J=8 Hz, 1H), 5.48 (m, 1H), 6.81 (d, J=8.4 Hz, 2H), 6.90 (d, J=8.4 Hz, 2H), 7.25–7.39 (m, 5H), 7.42 (t, J=8 Hz, 1H), 7.52 (d, J=8 Hz, 1H), 7.80 (d, J=8 Hz), 7.92 (s, 1H).

(B) Compound 38

Compound 37 (0.6 g, 1.1 mmol) in 10 mL MeOH was treated with 1 drop of 6N HCl and stirred at room temperature for two hours. The reaction was diluted with ethyl acetate and washed with 5 percent $NaHCO_3$ (2×) and dried over $MgSO_4$. The corresponding alcohol was obtained as a white wax (500 mg, 98 percent) after removal of the solvent:

TLC (R,0.55, 50 percent EA in H, UV or AmA). The benzylic alcohol (210 mg, 0.46 mmol) was oxidized to aldehyde Compound 38 (195 mg, 93 percent) with pyridinium dichromate [PDC; Corey et al., *Tetrahedron Lett.*, 5:399–402 (1979) (400 mg, 1.1 mmol) in dry DMF (4 mL) and purified by silica G column (35 percent EA in H): TLC (R,0.3, 25 percent EAZ in H, UV or AMA); NMR (CDCl$_3$, 400 MHz), δ1.42 (s, 9H), 2.97 (dd, J=5.6, 14 Hz, 1H), 3.12 (dd, J=6.4, 13.6 Hz, 1H), 4.98 (s, 2H), 5.36 (d, J=8 Hz, 1H), 5.49 (m, 1H), 6.80 (d, J=8.4 Hz, 2H), 6.92 (d, J=8.8 Hz, 2H), 7.31–7.38 (m, 5H), 7.61 (t, J=8 Hz, 1H), 8.06 (d, J=8 Hz, 1H) 8.14 (d, J=8 Hz, 1H), 8.34 (s, 1H), 10.03 (s, 1H).

(C) Compound 28

To a heterogeneous solution of AgO (124 mg, 1 mmol) in 2 mL 1N NaOH was added aldehyde Compound 38 in 4 mL MeOH. The reaction mixture was stirred at room temperature for 30 minutes. TLC showed disappearance of the starting material. The reaction mixture was diluted with ethyl acetate and the organic layer was washed with 1N HCl and dried over MgSO$_4$. The Boc-protected Compound 28 was obtained as a pale yellow powder (160 mg, 86 percent) after removal of the solvent and lyophilization. The protected Compound 28 (160 mg, 0.34 mmol) was dissolved in 15 mL dry ether and deprotected according to the Method B (2) to give Compound 28 as a white powder (110 mg, 80 percent, HCl salt): NMR (DMSO, 500 MHz),δ3.10 (m, 2H), 5.03 (s, 2H), 5.45 (br s, 1H), 6.86 (d, J=8.7 Hz, 2H), 7.03 (d, J=8.6 Hz, 2H), 7.34–7.43 (m, 5H), 7.64 (t, J=7.7 Hz, 1H), 8.21 (m, 2H), 8.38 (s, 1H), 8.48 (br m, 3H); HSMS: 376.1549 (M+H)$^+$, calcd for (C$_{23}$H$_{21}$NO$_4$+H) 376.1549.

EXAMPLE 20

Preparation of Compound 29

The title compound was prepared by first coupling Weinreb amide [Nahm et al., *Tetrahedron Lett.*, 22: 3815–3818 (1981); Angelastro et al., *J. Org. Chem.*, 54:3913–3916 (1989)] with 4-bromobenzotrifluoride according to Method G and deprotected according to Method B (2) to give Compound 29 as a pale yellow solid (HCl salt): NMR (DMSO, 400 MHz), δ3.13 (t, J=6.8 Hz, 2H), 5.02 (s, 2H), 5.44 (br s, 1H), 6.85 (d, J=8.6 Hz, 2H), 7.04 (d, J=8.6 Hz, 2H), 7.33–7.41 (m, 5H), 7.89 (d, J=8.2 Hz, 2H), 8.13 (d, J=8.2 Hz, 2H), 8.61 (br s, 3H); HRMS: 400.1540 (M+H)$^+$, calcd for (C$_{23}$H$_{20}$F$_3$NO$_2$+H$^{30}$) 400.1524.

EXAMPLE 21

Preparation of Compound 44 (Scheme 4)

(A) 3(S)-1,4-Diphenyl-2-oxo-3-amino-N-Boc-butane (Compound 40)

To a stirred solution of N-Boc-L-phenylalanine- N-methoxy-N-methylamide (Compound 39) (5.0 g, 14.5 mmol) in anhydrous THF (50 mL) under N$_2$ at zero degrees C was added 2.0M benzyl magnesium chloride in THF (21.7 mL, 43.5 mmol). The mixture was gradually warmed to room temperature and stirred for an additional three hours. The reaction mixture was then poured onto 1 N HCl (25 mL). The organic layer was separated and the aqueous layer was extracted with ether (3×35 mL). The combined organic layers were dried (MgSO$_4$) and concentrated to give a crude product. Purification of the crude material by flash chromatography ( EA:H; 1:4 ) afforded Compound 40 as a white solid (4.8 g, 98 percent R,0.3 (EA:H;1:4)); mp 86°–87° C.; [a]$^{24}_D$+31.22°(c 2.21, CH$_2$Cl$_2$); IR 3485, 2978, 1709, 1704, 1490, 1363, 1250 cm$^{-1}$; $^1$H-NMR (CDCl$_3$) δ1.14 (s, 9H), 2.9–3.15 2H), 3.65 (q, 2H, J=11.6 Hz), 4.61 (d, 1H, J=6.9 Hz), 5.1 (bs, 1H), 7.0–7.2 (m, 10H) ppm; $^{13}$C (CDCl$_3$) δ28.3, 37.8, 47.8, 59.5, 79.9, 127.0, 127.1, 128.8, 129.2, 129.6, 133.1, 135.2, 155.1, 206.5 ppm. HRMS: 472.0880, calcd for C$_{21}$H$_{25}$NO$_3$+Cs$^+$: 472.0880, (B) (2R, 3S) -1,4-Diphenyl-2-hydroxy-3-amino-N-Boc-butane (Compound 41)

To a stirred solution of Compound 40 (0.49 g, 1.4 retool) in anhydrous MeOH (1 mL) under N$_2$ at −22° C. was added NaBH$_4$ (0.16 g, 4.4 mmol). After 30 minutes, the mixture was gradually warmed to room temperature and then poured onto saturated NH$_4$Cl (10 mL). The mixture was extracted with ether (5×25 mL). The combined organic phase was washed with 1N HCl (2 ×25 mL), saturated NaHCO$_3$ (3×25 mL), dried (MgSO$_4$) and concentrated to give a crude product as a 9:1 mixture of diastereomers as determined by $^1$H-NMR. Recrystallization from benzene afforded Compound 41 as a crystalline white solid (0.42 g, 80 percent). R,0.26 (EA:H;1:4); mp 157–158° C.; [a]$^{25}_D$−10.12° (c 0.5, CH$_2$CL$_2$); IR 3691, 3155, 2927, 1794, 1706, 1471, 1381, 1166, 1096 cm$^{-1}$; $^1$H-NMR (CDCl$_3$, 300 MHz), δ1.35 (s, 9H), 2.55–3.05 (m, 4H), 3.83–4.0 (m, 2H), 4.65 (bs, 1H), 7.05–7.2 (m, 10H) ppm; $^{13}$C (CDCl$_3$ 125 MHz) δ28.3, 35.4, 40.3, 56.1, 74.8, 77.3, 126.4, 126.6, 128.4, 128.7, 129.3, 129.4, 138.1, 193.2 ppm. HRMS: 364.1902, calcd for C$_{23}$H$_{25}$NO$_3$+H$^{30}$: 364.1913.

The product was derivatized by treatment with SOCl$_2$ to give the 3,4-dibenzyl-oxazolidinone. [Kano et al., *Tetrahedron Lett.*, 28:6331–6334 (1987).] The assignment of stereochemistry was based on the vicinal coupling, J$_{3,4}$=5.0 Hz, consistent with that of the trans oxazolidinone.

(C) (2R, 3S)-1,4-Diphenyl-2-hydroxy-3-amino-butane HCl (Compound 44)

To a stirred solution of Compound 41 (0.20 g, 0.58 mmol) in CH$_2$CL$_2$ (5 mL) was added TFA (0.23 mL, 2.9 mmol). After 12 hours, the mixture was concentrated to give a crude white solid, which was taken up in 1N HCl (1 mL) and concentrated to give a crude product. This procedure was repeated three times. Recrystallization from ether/MeOH afford Compound 31 as a white crystalline solid (0.14 g, 87 percent): mp 158°–159° C.; [a]$^{25}_D$−11.83° (c 3.21, MeOH); $^1$H-NMR (CD$_3$OD, 300 MHz) δ2.6–2.8 (m, 3H), 3.05 (dd, 2H, J=10.0, 15.3 Hz), 3.2–3.3 (m, 1H), 3.43 (q, 2H, J=7.0 Hz), 3.88 (sept, 1H, J=3 Hz), 7.0–7.2 (m, 10H) ppm; $^{13}$C-NMR (CD$_3$OD, 125 MHz) δ33.9 40.0, 58.1, 72.9, 127.7, 128.5, 129.7, 130.2, 130.3, 130.4, 137.4, 139.4 ppm. HRMS: 264.6601, calcd for C$_{16}$H$_{20}$NO$^+$+Na$^+$: 264. 6611.

EXAMPLE 22

Preparation of Compound 45 (Scheme 4)

(A) (7S)-6-Oxo-7-amino-8-phenyl-N-Boc-octene (Compound 42)

To a stirred solution of Compound 39 (2.3 g, 7.4 mmol) in anhydrous ether (30 mL) under N$_2$ at zero degrees C was added freshly prepared pentene magnesium bromide (6.5 g, 37.3 mmol) in anhydrous ether (20 mL). The mixture was gradually warmed to room temperature and stirring was continued for 18 hours. The reaction mixture was poured onto 1N HCl (30 mL) at zero degrees C. The organic layer was separated and the aqueous layer was extracted with ether (4×25 mL). The combined organic phase was washed successively with 1N HCl×25 mL, saturated NaHCO$_3$ (2×25 mL), saturated NaCl (1×25 mL), dried over (MgSO$_4$), and concentrated to give a crude white solid. Purification by flash chromatography (EA:H;1:2) gave Compound 42 as a white crystalline solid (2.4 g, 98 percent). R$_f$0.7 (EA:H;1:1); mp 77.5–79° C.; [a]$^{25}$$_D$+50.58°(c 3.16 CH$_2$Cl$_2$); IR 3436, 2978, 2932, 1708, 1705, 1490, 1367, 1249, 1171 cm$^{-1}$; $^1$H-NMR (CDCl$^3$, 300 MHz) δ1.41 (s, 9H), 1.64 (s, 2H, J=6.8 Hz), 2.0 (q, 2H, J=7.1 Hz), 2.27–2.47 (m, 2H), 3.0 (dq, 2H, J=6.7, 13.9 Hz), 4.52 (q, 1H, J=7.1 Hz), 4.94–5.09 (m, 2H), 5.1(bd, 1H, J=7.1 Hz), 5.64–5.77 (m, 1H), 7.0–7.2 (m, 5H) ppm; $^{13}$C-NMR (CDCl$_3$, 125 MHz) δ22.2, 28.2, 32.8, 37.8, 39.8, 59.9, 79.7, 115.2, 126.9, 128.5, 129.1, 136.2, 137.7, 155.1, 209.1 ppm. HRMS: 450.1030, calcd for C$_{19}$H$_{27}$NO$_3$+Cs$^+$: 450.1045.

(B) (6S) -5-Oxo-6-amino-7-phenyl -N-Boc-heptanoic acid (Compound 43)

To a stirred solution of Compound 42 (0.23 g, 0.73 mmol) in acetone (20 mL) and water (20 mL) at room temperature was added NaIO$_4$ (0.62 g, 2.93 mmol) and KMnO$_4$ (0.07 g, 0.46 mmol). After an additional 12 hours of stirring the mixture was filtered and the resulting filtrate was concentrated. The concentrate was treated with 0.01 N NaOH (20 mL) and washed with ether (2×10 mL). The aqueous layer was then treated with 1N HCl until acidic. The aqueous layer was then extracted with ether (4×15 mL). These organic layers were combined, dried over (MgSO$_4$) and then concentrated to give a crude oil. Purification by chromatography (EA:H;4; 0.1 percent AcOH) afforded Compound 43 as a white solid (0.19 g, 78 percent). R$_f$0.2 (EA:H:0.1 percent AcOH); mp 88°–89° C.; [a]$^{25}$$_D$+8.32°(c 2.88, CH$_2$Cl$_2$); IR 3691, 3553, 2983, 1794, 1708, 1472, 1381, 1166, 1097 cm$^{31}$$^1$; $^1$H-NMR (CDCl$_3$, 300 MHz) δ1.37 (s, 9H), 1.75–1.90 (m, 2H), 2.2–2.6 (m, 4H), 2.9–3.1 (m, 2H), 4.55 (q, 1H), 5.1 (bd, 1H), 7.0–7.3 (m, 5H) ppm; $^{13}$C-NMR (CDCl$_3$, 125 MHz) δ18.1, 28.3, 32.7, 37.9, 39.5, 60.0, 80.1, 27.1, 128.7, 129.2, 136.1, 155.3, 178.2, 208.7 ppm. HRMS: 358.1630, calcd for C$_{18}$H$_{25}$NO$_5$+Na$^+$: 358.1630.

(C) (6S) -5-Oxo-6-amino-7-phenyl-heptanoic acid HCl (Compound 45)

To a stirred solution of Compound 43 (0.17 g, 0.5 mmol) in CH$_2$Cl$_2$ (3 mL) was added TFA (0.4 mL, 5.1 mmol). After 12 hours, the mixture was concentrated to give a crude white solid, which was taken up in 1N HCl (1 mL) and concentrated. This was repeated three times. The crude product was recrystallized from MeOH/EA to give Compound 45 as a white crystalline solid (0.12 g, 88 percent). mp 154–155° C.; [a]$^{25}$$_D$+10.68°(c 1.03, MeOH); $^1$H-NMR (D$_6$-DMSO, 300 MHz) δ1.5–1.8 (m, 2H), 2.15 (dt, 2H, J=2.2, 7.0 Hz), 2.4–2.6 (m, 2H), 3.1 (d, 2H, J=7.0 Hz), 3.34 (s, 4H), 4.36 (t, 1H, J=7.0 Hz), 7.25–7.30 (m, 5H) ppm; $^{13}$C-NMR (DMSO, 125 MHz) δ18.0, 32.4, 35.3, 38.94, 58.5, 127.3, 128.7, 129.4, 134.8, 174.0, 206.0 ppm. HRMS: 236.2801, calcd for C$_{12}$H$_{18}$NO$_3$Cl$^{30}$: 236.2870.

EXAMPLE 23

Preparation of Compound 27 (Scheme 5)

(A) (2S)-3-[4-(Benzyloxy)phenyl]-2-amino-N-Boc-propanol (Compound 48)

To a stirred solution of N-Boc-L-tyrosine (Compound 46; 4.0 gr, 14.2 mmol) in DMF (20 mL) at room temperature was added benzyl bromide (3.7 mL, 30.6 mmol), Cs$_2$CO$_3$ (13.9 gr, 42.6 mmol) and TBAI (25 mg, 0.07 mmol). Stirring was continued for 24 hours after which the reaction was taken up in EA (100 mL). The organic layer was washed with 1N HCl (3×20 mL), saturated NaHCO$_3$ (3×20 mL) and saturated NaCl (1×20 mL). The organic layer was dried (MgSO$_4$) and concentrated to give a crude yellow solid. Purification by flash chromatography (EA:H;1:4) afforded O-benzyl-L-tyrosine-N-Boc-benzyl ester (Compound 47) as a white solid (3.0 gr, 46 percent). $^1$H NMR (500 MHz, CDCl$_3$) δ1.42 (s, 9 H), 3.0 (d, 2H, J=3.1 Hz), 4.58 (q, 1H, J=5.8 Hz), 4.97 (q, 1H, J=8.3 Hz), 5.0 (s, 2H), 5.15 (q, 2H, J=12.3 Hz), 6.9 (AB, 4H, J=8.4, 53.5 Hz), 7.29–7.43 (m, 5H) ppm; $^{13}$C NMR (125 MHz, CDCl$_3$) δ28.3, 37.3, 54.5, 67.0, 69.9, 79.9, 114.8, 127.4, 127.9, 128.4, 128.5, 130.3, 135.0, 136.9, 155.1, 157.8, 171.7 ppm.

To a stirred solution of Compound 47 (2.7 gr, 5.9 mmol) in anhydrous THF (15 mL) at room temperature under N$_2$ was add LiBH$_4$ (0.07 gr, 3.2 mmol). After two hours the reaction mixture was poured onto 1N HCl (5 mL) and then taken up in EA (50 mL). The organic layer was washed with 1N HCl (3×5 mL), saturated NaHCO$_3$ (3×5 mL) and saturated NaCl (1×5 mL). The organic layer was dried (MgSO$_4$) and concentrated to give a crude white solid. Purification by flash chromatography (EA:H;4) afforded the Compound 48 as a white solid (2.0 gr, 97 percent). $^1$H NMR (500 MHz, CDCl$_3$) δ1.42 (s, 9H), 2.78 (d, 2H, J=6.8 Hz), 2.84 (br s, 1H), 3.53–3.62 (m, 1H), 3.63–3.65 (m, 1H), 3.82 (bs, 1H), 4.86 (br s, 1H), 5.03 (s, 2H), 6.9 (AB, 4H, J=8.5, 53.9 Hz), 7.29–7.43 (m, 5H) ppm; $^{13}$C NMR (125 MHz, CDCl$_3$) δ28.3, 36.3, 54.5, 64.8, 79.6, 114.8, 127.4, 127.9, 128.5, 128.5, 130.3, 136.9, 157.8 ppm.

(B) (2S)-O-Tosyl-3-[4-(benzyloxy)phenyl]-2-amino-N-Boc-propanol (Compound 49)

To a stirred solution of Compound 48 (2.0 gr, 5.6 mmol) in anhydrous CH$_2$Cl$_2$ (10 mL) at zero degrees C. under N$_2$ was added Et$_3$N (1.2 mL, 8.4 mmol), DMAP (cat.) and tosyl chloride (1.4 gr, 7.3 mmol). After 5 hours, the reaction mixture was washed with 1N HCl (2×5 mL), saturated NaHCO$_3$ (2×5 mL) and saturated NaCl (1×5 mL). The organic layer was dried (MgSO$_4$) and concentrated to give a crude yellow solid. Purification by flash chromatography gave the Compound 49 as a white solid (2.2 gr, 79 percent). $^1$H NMR (300 MHz, CDCl$_3$) δ1.40 (s, 9H), 2.45 (s, 3H), 2.60–2.81 (m, 2H), 3.75–4.0 (m, 3H), 4.7 (bd, 1H, J=7.5 Hz), 5.0 (s, 2H), 6.92 (AB, 4H, J=8.4, 45.4 Hz), 7.34 (dd, 6H, J=6.5, 8.2, 15.9 Hz), 7.78 (d, 2H, J=8.5 Hz) ppm.

(C) (2S)-S-Acetate-3-[4-benzyloxy)phenyl]-2-amino-N-Boc-propanethiol (Compound 50)

To a stirred solution of Compound 49 (2.1 gr, 4.2 mmol) in anhydrous DMF (10 mL) at zero degrees C. under N$_2$ was added potassium thioacetate (0.6 gr, 5.04 mmol). After three hours, the reaction was gradually allowed to warm to room temperature. After an additional 8 hours of stirring at room temperature, the reaction mixture was taken up in EA (50 mL). The organic layer was washed with 1N HCl (3×20 mL), saturated NaHCO$_3$ (3×20 mL) and saturated NaCl (1×20 mL). The organic layer was dried (MgSO$_4$) and concentrated to afford a crude brownish solid. Recrystallization from EA/H gave the Compound 50 as white solid (1.6 gr, 93 percent). $^1$H NMR (CDCl$_3$, 500 MHz) δ1.39 (s, 9H), 2.35 (s, 3H), 2.70 (dd, 1H, J=3.6, 6.6 Hz), 2.73–2.89 (m, 2H), 2.91 (dd, 1H, J=4.0, 7.0 Hz), 3.93 (bs, 1H), 4.56 (bs, 1H), 5.03 (s, 2 H), 7.02 (AB, 4H, J=4.4, 38.0 Hz), 7.31–7.51 (m, 5H) ppm. HRMS: 548.0888, Calcd for C$_{23}$H$_{29}$NSO$_4$ +Cs$^+$: 548.0872.

(D)
(2S)-3-[4-(benzyloxy)phenyl]-2-amino-propanethiol HCl Compound 27)

To a stirred solution of Compound 50 (0.1 gr, 0.24 mmol) in ethanol (5 mL) at zero degrees C. was added 1N NaOH solution (0.48 mL, 0.48 mmol). After one hour the reaction mixture was gradually warmed to room temperature and stirred for an additional 3 hours. The reaction mixture was then taken up in EA (50 mL). The organic solution was washed 1N HCl (3×25 mL), saturated NaHCO$_3$ (3×25 mL) and saturated NaCl (1×25 mL). The organic layer was dried (MgSO$_4$) and concentrated to give a crude white solid of Compound 51 (0.09 gr, >99 percent). R$_f$0.31 (EA:H;1:4); $^1$H NMR (300 MHz, CDCl$_3$) δ1.41 (s, 9H), 2.5–2.9 (m, 4H), 3.95 (bs, 1H), 4.72 (bs, 1H), 5.03 (s, 2H), 6.9–7.1 (AB, 4 H), 7.3–7.5 (m, 5H) ppm.

The crude white solid Compound 51 (0.09 gr, 2.8 mmol) was taken up in ether (1 mL). To the stirred solution was added a saturated HCl (g)/ether solution (10 mL). After 24 hours of stirring at room temperature, the solvent was removed to a give another crude white solid. Recrystallization from MeOH/ether afforded the Compound 27 as a white solid (0.03 gr, 34 percent). $^1$H NMR (300 MHz, DMSO-d$_6$) δ2.62 (dd, 1H, J =6.2, 14.7 Hz), 2.82 (dd, 1H, J=4.6, 14.7 Hz), 2.84–295 (m, 2H), 3.52 (p, 1H, J=7.0 Hz), 5.07 (s, 2H), 6.97 (AB, 4H, J=8.6, 19.8 Hz), 7.3–7.45 (m, 5H) ppm. HRMS: 274.1258, Calcd for C$_{16}$H$_{20}$NSO (M$^{30}$): 274.1266. Anal Calcd for C$_{16}$H$_{20}$NSOCl: C 62.02 percent, H 6.51 percent, N 4.52 percent, S 10.34 percent. Found C 62.11 percent, H 6.59 percent, N 4.31 percent, S 10.00 percent.

(E) preparation of Compound 27a (Scheme 5) (1) Di-((2S)-3-[4-(benzyloxy)phenyl]-2-amino-N-Boc-propane)-disulphide (Compound 51a)

To a stirred solution of Compound 50 (0.3 g, 0.72 mmol) in ethanol (5 mL) at zero degrees C was added 1 N NaOH solution (1.44 mL, 1.42 retool). After one hour, the reaction mixture was gradually warmed to room temperature, and stirred for an additional 3 hours. Then an I$_2$/ethanol solution was added until a yellowish solution persisted, and stirring was continued for 30 minutes. The reaction mixture was then taken up in EA (100 mL). The organic solution was washed with a 20 percent Na$_2$S$_2$O$_3$ solution until the organic layer was clear, followed by 1N HCl (3×25 mL), saturated NaHCO$_3$ (3×25 mL) and saturated NaCl (133 25 mL). The organic layer was dried (MgSO$_4$) and concentrated to give a crude white solid. Recrystallization from EA/ether afforded Compound 51a as a white solid (0.22 g, 97 percent). $^1$H NMR (CDCl$_3$, 300 MHz) δ1.41 (s, 18H), 2.7–3.0 (m, 8H), 4.0–4.1 (bs, 2H), 5.03 (s, 2H), 7.0 (AB, 8H, J=8.5, 58,1 Hz), 7.25–7.3 (m, 10H) ppm.

(2) Di-((2S)-3-[4-(benzyloxy)phenyl]-2-amino-propane)-disulphide HCl (Compound 27a )

To a stirred solution of Compound 51a (0.2 g, 1.6 retool) in ether (5 mL) was added a saturated HCl (g)/ether solution (10 mL). After 24 hours, the resulting precipitate was isolated by filtration and recrystalization from MeOH/ether to afford Compound 27a as a white solid (0.06 g, 30 percent). $^1$H NMR (500 MHz, CD$_3$OD) δ2.78–2.88 (m, 4H), 2.9 (dd, 2H, J=4.2, 7.0 Hz), 3.01 (dd, 2H, J=3.0, 7.0), 3.75–3.77 (bs, 2H), 5.1 (s, 4H), 7.1 (AB, 8H, J=4.3, 34.0 Hz), 7.34–7.45 (m, 5H) ppm. HRMS: 545.2311, Calcd for C$_{23}$H$_{38}$N$_2$S$_2$O$_2$Cl$_2$+H$^+$: 545.2296.

EXAMPLE 24

Preparation of Compound 54

(A) (2S)-1-[4-(Benzyloxy)phenyl]-6-phenyl-2-amino-3-oxo-N-Boc-hexane-(Compound 53 )

To a stirred solution of N-Boc-O-benzyl-L-tyrosine-N-methoxy-N-methylamide (Compound 52; 1.5 gr, 3.62 mmol) in anhydrous THF (10 mL) under N$_2$ at room temperature was added freshly prepared 3-phenyl-propane magnesium bromide (10.9 mmol) in anhydrous THF (10 mL). Stirring was continued for 3 hours after which time the reaction was poured onto 1N HCl (30 mL). The organic layer was separated and the aqueous layer was extracted with EA (4×25 mL). The combined organics were washed with 1N HCl (3×25 mL), saturated NaHCO$_3$ (3×25 mL) and saturated NaCl (1×25 mL). The organic layer was dried (MgSO$_4$) and concentrated to give a crude yellowish solid. Recrystallization from EA:H (1:15) gave Compound 53 as a white crystalline solid (1.35 gr, 80 percent). mp 128°–129° C.; $^1$H NMR (CDCl$_3$, 500 MHz) ≠7 1.40 (s, 9H), 1.78–1.95 (m, 2H), 2.25–2.48 (m, 2H), 2.56 (t, 2H, J =14.0 Hz), 2.96 (dd, 1H, J=6.8, 14.0 Hz), 4.46 (q, 1 H, J=7.5 Hz), 5.05 (s, 2H), 5.10 (d, 1H, J=7.5 Hz), 6.88–7.13 (AB, 4H), 7.2–7.4 (m, 10H) ppm; $^{13}$C (CDCl$_3$, 125 MHz) δ24.7, 28.3, 34.9, 37.0, 40.0, 60.1, 70.0, 79.0, 114.9, 125.9, 127.4, 128.4, 128.5, 128.6, 130.2, 136.9, 141.3, 155.15, 157.77, 209.16 ppm. HRMS: 472.2490, Calcd for C$_{30}$H$_{33}$NO$_4$ +H$^+$: 472.2488.

(B) (2S)-1-[4-(Benzyloxy)phenyl]-6-phenyl-2-amino-3-oxo-hexane HCl (Compound 54)

To a stirred solution of Compound 53 (0.1 gr, 0.21 mmol) in ether (5 mL) at room temperature was added a saturated HCl (g)/ether solution (20 mL). After 24 hours of stirring, the resulting precipitate was isolated by filtration. The crude product was recrystallized from MeOH/ether to give the Compound 54 as hard white crystals (0.065 gr, 75 percent). $^1$H NMR (300 MHz, DMSO-d$_6$) δ1.65–1.78 (m, 2H), 2,49–2.55 (m, 4 H), 3.0 (d, 2H, J=6.5 Hz), 4.31 (t, 1H, J=6.5 Hz), 5.07 (s, 2H), 6.92–7.8 (m, 14H), 8.2 (br s, 3H) ppm; $^{13}$C NMR (125 MHz, DMSO-D$_6$) δ24.4, 34.6, 34.8, 58.7, 68.2, 115.0, 125.9, 126.8, 127.7, 127.8, 128.3, 128.4, 128.5, 130.6, 137.1, 157.8, 208.3 ppm. HRMS: 374.2106, Calcd for C$_{25}$H$_{28}$NO$_2$Cl+H$^+$: 374.2120. Anal Calcd for C$_{25}$H$_{28}$NO$_2$Cl: 73.25 percent, H 6.88 percent, N 3.42 percent. Found C 73.25 percent, H 6.81 percent, N 3.40 percent.

EXAMPLE 25

Preparation of Compound 60 (Scheme 6)

(A) O-(2-Naphthylmethyl)-L-tyrosine-N-Boc-(2-naphthylmethyl) ester (Compound 55)

To a stirred solution of N-Boc-L-tyrosine (Compound 46) 6.1 gr, 21.4 mmol) in DMF (30 mL) at room temperature was added 2-(bromomethyl)naphthalene (10.4 gr, 47.0 mmol), $Cs_2CO_3$ (17.4 gr, 53.4 mmol) and TBAI (25 mg, 0.07 mmol). Stirring was continued for 48 hours after which the reaction was taken up in EA (200 mL). The organic layer was washed with 1N HCl (3×240 mL), saturated $NaHCO_3$ (3×40 mL) and saturated NaCl (1×40 mL). The organic layer was dried ($MgSO_4$) and concentrated to give a crude brown oil. Recrystallization from MeOH afforded Compound 55 as a white solid (5.0 gr, 42 percent). m.p. 99.5°–101° C.; $^1$H NMR ($CDCl_3$, 300 MHz) δ1.41 (s, 9H), 3.02 (d, 2H, J=5.7 Hz), 4.62 (q, 1H, J=Hz), 5.01 (br d, 1H, J=Hz), 5.07 (s, 2H), 5.23 (d, 1H, J=12.2 Hz), 5.34 (d, 1H, J=12.3 Hz), 6.83 (AB, 4H, J=8.4, 43.2 Hz), 7.4–7.53 (m, 6H), 7.8–7.99 (m, 8H) ppm; $^{13}$C NMR ($CDCl_3$, 125 MHz) δ 28.3, 38.3, 55.0, 67.2, 70.2, 78.2, 125.3, 126.1, 126.2, 126.3, 126.4, 126.5, 127.7, 127.8, 127.9, 128.1, 128.4, 130.4, 132.6, 133.07, 133.13, 133.19, 133.29, 134.48, 157.85, 171.57 ppm. HRMS: 694.1570, Calcd for $C_{36}H_{35}NO_5 +Cs^+$: 694.1570.

(B) (2S)-3-[4-(2-Naphthylmethyloxy)phenyl]-2-amino-N-Boc-propanol (Compound 56)

To a stirred solution of Compound 55 (1.5 gr, 2.6 retool) in anhydrous THF (25 mL) at room temperature under $N_2$ was added $LiBH_4$ (0.058 gr, 2.67 mmol). After 18 hours the reaction mixture was poured onto 1N HCl (10 mL). The solvent was reduced and the resulting slurry was taken up in EA (50 mL). The organic layer was washed with 1N HCl (3×25 mL), saturated $NaHCO_3$ (3×25 mL) and saturated NaCl (1×25 mL). The organic layer was dried ($MgSO_4$) and concentrated to give a crude white solid. Purification by flash chromatography (EA:H;1:4) afforded Compound 56 as a white solid (1.0 gr, 96 percent). $R_f$ 0.44 (EA:H;1:1): m.p. 138°–139° C.; $[a]^{25}_D$ –13.89°(c 18, $CH_2Cl_2$); 1H NMR ($CDCl_3$, 300 MHz) δ1.40 (s, 9H), 2.76 (d, 2H, J=7.2 Hz), 3.51 (dd, 1H, J=5.1, 10.9 Hz), 3.63 (dd, 1H, J=3.6, 11.2 Hz), 3.8 (bs, 1H), 4.78 (bd, 1H, J=7.8 Hz), 5.18 (s, 2H), 7.0 (AB, 4H, J=8.4, 53.1 Hz), 7.4–7.6 (m, 3H), 7.7–7.9 (m, 4H) ppm. HRMS: 540.1153, Calcd for $C_{25}H_{29}NO_4+Cs^+$: 540.1151. Anal Calcd for $C_{25}H_{229}NO_4$: C 73.68 percent, H 7.17 percent, N 3.43 percent. Found C 73.60 percent, H 7.21 percent, N 3.61 percent.

(C) (2S)-O-Mesyl-3-[4-(2-naphthylmethyloxy)phenyl]-2-amino-N-Boc-propanol (Compound 57)

To a stirred solution of Compound 56 (1.0 gr, 2.45 mmol) in anhydrous $CH_2Cl_2$ (20 ml) at zero degrees C. under $N_2$ was added $Et_3N$ (0.52 mL, 3.7 retool), DMAP (cat.) and mesyl chloride (0.29 mL, 3.7 mmol). After one hour, the reaction was quenched by addition of $H_2O$ (5 mL). The organic layer was separated and the aqueous layer was extracted with $CH_2Cl_2$ (3×10 mL). The combined organics were washed with 1N HCl (2×20 mL), saturated $NaHCO_3$ (2×20 mL) and saturated NaCl (1×20 mL). The organic layer was dried ($MgSO_4$) and concentrated to give a white solid. Purification by flash chromatography (EA:H;1:2) afforded Compound 57 as a white solid (0.92 gr 78 percent. m.p. 112.5°–113 5° C.; $[a]^{25}_D$ –12.03 (c 1.33, $CH_2Cl_2$); 1H NMR (300 MHz, $CDCl_3$) δ1.41 (s, 9H), 2.78–2.82 (m, 2H), 2.99 (s, 3H), 4.0–4.25 (m, 3H), 4.6–4.65 (bd, 1H), 5.2 (s, 2H), 6.9–7.2 (m, 4H), 7.45–7.08 (m, 3H), 7.8–7.9 (m, 4H) ppm; $^{13}$C (125 MHz, $CDCl_3$) δ28.3, 37.2, 36.25, 50.9, 69.7, 70.2, 115.2, 125.2, 126.3, 126.4, 127.7, 127.9, 128.4, 128.9, 130.3, 133.1, 133.3, 134.4, 157.8 ppm. HRMS:485.1870, Calcd for $C_{26}H_{31}NSO_6$ ($M^+$): 485.1872.

(D) (2S)-3-[4-(2-Naphthylmethyoxy)phenyl-2-amino-N-Boc-azido-propane (Compound 58)

To a stirred solution of mesylate (Compound 57) (0.9 gr, 1.85 retool) in DMF (10 mL) at 60° C. was added $NaN_3$ (0.72 gr, 11.1 mmol). After 3 hours the reaction mixture was taken up in EA (50 mL) and then washed with 1N HCl (2×20 mL), saturated $NaHCO_3$ (2×20 mL) and saturated NaCl (1×20 mL). The organic layer was dried ($MgSO_4$) and concentrated. The crude white solid was purified by flash chromatography to give Compound 58 as a white solid (0.6 gr, 76 percent). m.p. 141°–142° C.; $[a]^{25}_D$ –5.8°(c 1.72, $CH_2Cl_2$); $^1$H NMR 500 MHz $CDCl_3$) δ1.44 (s, 9H), 2.7–2.78 (dd 1H, J=8.0, 14.0 Hz), 2.8–2.9 (d, 1H, J=6.0 Hz), 3.28–3.33 (dd, 1H, J=4.0, 12.0Hz), 3.41–3.49 (m, 1H), 3.94 (s, 1H), 4.68 (bd, 1 H, J=7.0 Hz), 5.22 (s, 3H), 6.95–7.2 (AB, 4H, J =8.0, 75.0 Hz), 7.48–7.76 (m, 3H), 7.8–7.9 (m, 4H) ppm; $^{13}$C (125 MHz, $CDCl_3$) δ28.3, 37.2, 51.4, 53.0, 79.68, 115.0, 125.2, 126.0, 126.2, 126.3, 127.7, 127.9, 128.3, 129.4, 130.3, 133.0, 133.2, 134.4, 155.0, 157.6 ppm; IR (KBr) 3373, 2981, 2943, 2861, 2361, 2103, 1683, 1611, 1510, 1288, 1242, 1167 $cm^{-1}$. HRMS:429.2139, Calcd for $C_{25}H_{30}N_2O_3+Na^+$: 429.2154.

(E) (2S)-3-[4-(2-Naphthylmethyloxy)phenyl]-1,2-diamino-N-Boc-propane. (Compound 59)

To a stirred solution of Compound 58 (0.11 gr, 0.27 mmol) in anhydrous THF (5 mL) at room temperature under $N_2$ was added $LiAlH_4$ (0.010 gr, 0.26mmol). After 30 minutes, 1N HCl (1 mL) was added to the reaction mixture. The reaction mixture was concentrated and then taken up in 1N NaOH (3 mL). The aqueous layer was extracted with $CH_2Cl_2$ (4×10 mL). The combined organics were washed with saturated NaCl (2×10 mL), dried ($MgSO_4$) and concentrated to give a white solid. Purification by flash chromatography ($CH_2Cl_2$: $Et_3N$;10:0.5) afforded Compound 59 as a white solid (0.07 gr, 63 percent). $^1$H NMR (300 MHz, $CDCl_3$) δ1.41 (s, 9H), 2.58 (dd, 2H, J=6.8, 13.1 Hz), 2.72 (dt, 2H, J=8.6, 13.2 Hz), 3.75 (bs, 1H), 4.73 (bd, 1H, J=8.6 Hz), 5.19 (s, 2H), 6.9–7.2 (AB, 4H), 7.4–7.6 (m, 3H), 7.8–7.9 (m, 4H) ppm; $^{13}$C NMR (500 MHz, $CDCl_3$) δ28.3, 37.9, 44.5, 54.0, 70.1, 114.8, 125.2, 126.0, 126.2, 126.3, 127.7, 127.9, 128.3, 130.2, 133.0, 133.2, 134.5, 155.8, 157.4 ppm. HRMS: 429.2139, Calcd for $C_{25}H_{30}N_2O_3+Na^+$: 429.2154.

(F) (2S)-3-[4-(2-Naphthylmethyloxy) phenyl]-1,2-diamino-propane HCl (Compound 60)

To Compound 59 (0.06 gr, 0.15 mmol) suspended in ether (1 mL) was add a saturated solution of HCl (g)/ether (5 mL). After 24 hours the reaction mixture was concentrated and the crude solid recrystallized from MeOH/ether to give the desired product Compound 60 as a white solid (0.02 gr, 34 percent). $^1$H NMR (500 MHz, $CD_3OD$) δ2.92 (dd, 1H, J=8.1, 14.7 Hz), 3.03 (dd, 1 H, J=7.0, 14.8 Hz), 3.19 (dd, 1H, J=5.6, 14.0 Hz), 3.27 (dd, 1H, J=7.1, 13.9 Hz), 3.75 (p, 1H, J=7.0 Hz), 5.27 (s, 2H), 7.12 (AB, 4H, J=9.0, 103.3 Hz), 7.42–7.61 (m, 3H), 7.82–7.90 (m, 4H) ppm.

HRMS:307.1810, Calcd for $C_{20}H_{24}N_2O+H^+$: 307.1810.

Enzymatic Assays and Inhibition Analysis Based on the Amidase Activity

Procedures and conditions for the enzymatic assays, kinetic analyses, and inhibition studies are essentially the same as previously reported and indicated in Table 2.

Inhibition of the epoxide hydrolase activity of $LTA_4$ hydrolase

Aliquots of enzyme (2.5 mg) were preincubated for 30–40 minutes at room temperature in 100 mL of 50 mM HEPES, pH 8, containing various amounts of the respective inhibitor. Each compound was added to the buffer in DMF (final conclusion <0.25 percent) and in the case of Compound 27, 1 mM dithiothreitol (DTT) was also included in the incubation buffer. Samples were further incubated with 20–25 mM $LTA_4$ for 15 seconds at room temperature and the reactions were terminated by the addition of 2 volumes of MeOH. After addition of 200 ng $PGB_1$ (internal standard), samples were acidified to pH value of 3 with 0.1M HCl, extracted on Chromabond C18 columns (Mackerey & Nagel), and finally analyzed on a computerized Waters HPLC system. The column (Radial-Pak $C_{18}$ cartridge, 100×5 mm, Waters) was eluted with a mixture of methanol/water/acetic acid (70:30:0.01, v/v) at a flow rate of 1.2 mL/minutes. The UV absorbance of the eluate was monitored continuously at 270 nm. Amounts of $LTB_4$ were computer calculated from peak area ratios between $LTB_4$ and the internal standard $PGB_1$. Peak area ratios were converted into molar ratios from comparisons with standard curve constructed from injections of known amounts of the respective compound.

The foregoing description and the examples are intended as illustrative and are not to be taken as limiting. Still other variations within the spirit and scope of this invention are possible and will readily present themselves to those skilled in the art.

We claim:

1. A process of inhibiting the activity of the enzyme leukotriene $A_4$ hydrolase comprising admixing in an aqueous medium said enzyme and a substrate therefor with an inhibiting amount of an inhibitor compound for that enzyme under biochemical reaction conditions, and maintaining the resulting admixture under biochemical reaction conditions for a time period sufficient for the activity of said enzyme to be inhibited, said inhibitor compound having a structure that corresponds to the formula

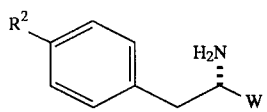

wherein the depicted —$NH_2$ group is in the (S) configuration; —W is —$CH_2SH$, —$CH_2NH_2$ or C(=Z)—Y, wherein =Z is =O, or —H and —OH; and —Y selected from the group consisting of (a) phenyl, (b) trifluoromethylphenyl, (c) carboxyphenyl, (d) benzyl, (e) $C_1$–$C_6$ alkylenecarboxyl, (f) $C_1$–$C_6$ alkyl, (g) $C_2$–$C_6$ alkenyl, (h) $C_1$–$C_6$ alkylenephenyl and (i) —C(=O)—X—$R^1$ wherein X is O or NH and, $R^1$ is selected from the group consisting of $C_1$–$C_6$ alkyl, $C_1$–$C_6$ alkylenecarboxyl, and benzyl;

$R^2$ is hydrogen, benzyloxy or 2-naphthylmethyloxy, and a pharmaceutically acceptable acid addition salt thereof.

2. The process according to claim 1 wherein $R^2$ is benzyloxy.

3. The process according to claim 2 wherein said inhibitor compound contains two phenyl rings.

4. The process according to claim 1 wherein —W is —$CH_2SH$ or —$CH_2NH_2$.

5. The process according to claim 1 wherein W is C(=Z)—Y.

6. The process according to claim 5 wherein =Z is =O.

7. The process according to claim 6 wherein —Y is —C(=O)—X—$R^1$.

8. The process according to claim 5 wherein =Z is —H and —OH, and said —OH is in the (S) configuration.

9. A process of inhibiting the activity of the enzyme leukotriene $A_4$ hydrolase comprising admixing in an aqueous medium said enzyme and a substrate therefor with an inhibiting amount of an inhibitor compound for that enzyme under biochemical reaction conditions, and maintaining the resulting admixture under biochemical reaction conditions for a time period sufficient for the activity of said enzyme to be inhibited, said inhibitor compound having a structure that corresponds to the formula

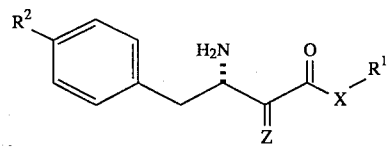

wherein the depicted —$NH_2$ group is in the (S) configuration;

X is O or NH;

$R^1$ is selected from the group consisting of $C_1$–$C_6$ alkyl, $C_1$–$C_6$ alkylenecarboxyl and benzyl;

$R^2$ is hydrogen, benzyloxy or 2-oxynaphthmethyl;

=Z is =O, or —H and —OH; and a pharmaceutically acceptable acid addition salt thereof.

10. The process according to claim 9 wherein =Z is —H and —OH, and said —OH in the (S) configuration.

11. The process according to claim 9 wherein =Z is =O.

12. The process according to claim 11 wherein said inhibitor compound has a structure that corresponds to the formula

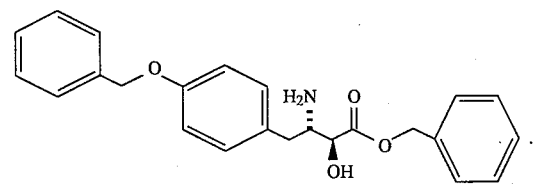

13. The process according to claim 9 wherein said compound is provided as a pharmaceutical composition dissolved or dispersed in a pharmaceutically acceptable diluent.

14. A process of inhibiting the activity of the enzyme leukotriene $A_4$ hydrolase comprising admixing in an aqueous medium said enzyme and a substrate therefor with an inhibiting amount of an inhibitor compound for that enzyme under biochemical reaction conditions, and maintaining the resulting admixture under biochemical reaction conditions for a time period sufficient for the activity of said enzyme to be inhibited, said inhibitor compound having a structure that corresponds to the formula

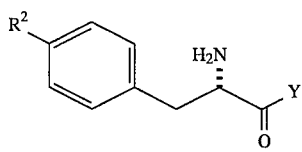

wherein the depicted —NH$_2$ group is in the (S) configuration;

—Y is selected from the group consisting of (a) phenyl, (b) trifluoromethylphenyl, (c) carboxyphenyl, (d) benzyl, (e) C$_1$–C$_6$ alkylenecarboxyl, (f) C$_1$–C$_6$ alkyl, (g) C$_2$–C$_6$ alkenyl, (h) C$_1$–C$_6$ alkylenephenyl;

R$^2$ is hydrogen, benzyloxy or 2-naphthylmethyloxy, and a pharmaceutically acceptable acid addition salt thereof.

15. The process according to claim 14 wherein said inhibitor compound contains three phenyl rings.

16. The process according to claim 15 wherein R$^2$ is benzyloxy.

17. The process according to claim 16 wherein said inhibitor compound has a structure that corresponds to the formula

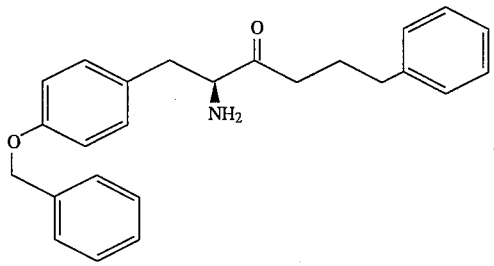

18. A process for treating inflammation in a mammal that comprises administering to a mammal having inflammation a leukotriene A$_4$-inhibiting amount of a leukotriene A$_4$ inhibitor compound whose structure corresponds to the formula

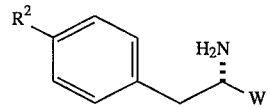

wherein the depicted -NH$_2$ group is in the (S) configuration;

—W is —CH$_2$SH, —CH$_2$NH$_2$ or C(=Z)—Y, wherein =Z is =O, or —H and —OH; and —Y is selected from the group consisting of (a) phenyl, (b) trifluoromethylphenyl, (c) carboxyphenyl, (d) benzyl, (e) C$_1$–C$_6$ alkylenecarboxyl, (f) C$_1$–C$_6$ alkyl, (g) C$_2$–C$_6$ alkenyl, (h) C$_1$–C$_6$ alkylenephenyl and (i) —C(=O)—X—R$^1$ wherein X is O or NH and, R$^1$ is selected from the group consisting of C$_1$–C$_6$ alkyl, C$_1$–C$_6$ alkylenecarboxyl, and benzyl;

R$^2$ is hydrogen, benzyloxy or 2-naphthylmethyloxy, and a pharmaceutically acceptable acid addition salt thereof.

19. The process according to claim 18 wherein R$^2$ is benzyloxy.

20. The process according to claim 19 wherein said leukotriene A$_4$ inhibitor compound contains three phenyl rings.

* * * * *